US007001743B2

(12) United States Patent
Cosgrove et al.

(10) Patent No.: US 7,001,743 B2
(45) Date of Patent: Feb. 21, 2006

(54) EXPANSIN POLYNUCLEOTIDES, RELATED POLYPEPTIDES AND METHODS OF USE

(75) Inventors: Daniel J. Cosgrove, University Park, PA (US); Yajun Wu, Logan, UT (US)

(73) Assignee: The Penn State Research Foundation, University Park, PA (US)

( * ) Notice: Subject to any disclaimer, the term of this patent is extended or adjusted under 35 U.S.C. 154(b) by 372 days.

(21) Appl. No.: 10/125,001

(22) Filed: Apr. 18, 2002

(65) Prior Publication Data

US 2003/0054533 A1 Mar. 20, 2003

Related U.S. Application Data

(60) Provisional application No. 60/285,050, filed on Apr. 19, 2001.

(51) Int. Cl.
*C12P 21/06* (2006.01)
*A61K 35/78* (2006.01)

(52) U.S. Cl. ...................... 435/69.1; 530/370; 800/278; 800/295; 435/419

(58) Field of Classification Search ................ 435/69.1, 435/419, 468; 530/370, 300; 800/278, 295, 800/290, 298
See application file for complete search history.

(56) References Cited

U.S. PATENT DOCUMENTS

| | | | |
|---|---|---|---|
| 3,844,890 A | 10/1974 | Horikoshi et al. | |
| 3,966,543 A | 6/1976 | Cayle et al. | |
| 4,004,976 A | 1/1977 | Isaac | |
| 5,175,275 A | 12/1992 | Dobashi et al. | |
| 5,959,082 A | 9/1999 | Cosgrove et al. | |
| 5,990,182 A | 11/1999 | Hosoya et al. | |
| 5,990,283 A | 11/1999 | Cosgrove et al. | |
| 6,184,440 B1 | 2/2001 | Shoseyou et al. | |
| 2003/0167506 A1 * | 9/2003 | Multani et al. ............. | 800/278 |

FOREIGN PATENT DOCUMENTS

WO   WO 01/88163   11/2001

OTHER PUBLICATIONS

Bowie et al, Science 247:1306–1310.*
McConnell et al, Nature 411 (6838):709–713, 2001.*
Fourgoux–Nicol et al. (1999, Plant Molecular Biology 40: 857–872).*
Cosgrove et al (1997, PNAS 94(12):6559–6564).*
Bayer, E.A., et al., Current Opinion in Structural–Biology 8:548–557 (1998).
Brenner, et al., PNAS vol. 95, pp. 6073–6078 (May 1998).
Broadwater, et al., Zea mi, the maize homolog of the allergen–encoding Loi pi gene of rye grass:, Gene, 131:227–230 (1993).
Cleland, R.E., Planta 170:379–385 (1987).
Cosgrove, D.J. et al. "Group I allergens of grass pollen as cell wall–loosening agents", Proc. Natl. Acad. Sci. USA 94:6559–6564 (1997).
Cosgrove, et al., "Role of expansin in cell enlargement of oat coleoptiles", Plant Physiol. 103:1321–1328 (1993).
Cosgrove, "Characterization of long–term extension of isolated cell walls from growing cucumber hypocotyls", Planta vol. 177:121–130 (1989).
Crowell, "Cytokinin regulation of a soybean pollen allergen gene", Plant Mol. Bio. 25:829–835 (1994).
Dahlyat, et al., "DeNovo protein design: fully automated sequence selection", Science, 278:82–87 (1997).
DeGrado, "Proteins from Scratch", Science, 278:80–81 (1997).
Deutscher, M.P., Academic Press 1990, Guide to Protein Purification, pp. 174–193.
Esch, et al., "Identification and Localization of Allergenic Determinants on Grass Group I Antigens Using Monoclonal Antibodies", J. Imm. 142(1):179–184 (1989).
Fry, Stephen C., Current Biology 4(9):815–817 (1994).
Fry, Stephen C., Physiologia Plantarium, 75:532–535 (1989).
Griffith, et al., Cloning and sequencing of Loi, pi, the major allergenic protein of rye–grass pollen:, FEBS 09407, vol. 279(2):210–215 (1991).
Heslop–Harrison, et al., "The pollen–stigma interaction in the grasses", Acta Bot. Neercl. 4(2):193–211 (1985).
Heslop–Harrison, et al., "The pollen–stigma interaction in the grasses", Acta Bot. Neercl. 33(1):81–99 (1984).
Knox, et al., "Environmental and molecular biology of pollen allergens", Trends in Plant Science, vol. 1(5) 156–164 (1996).
Knox, et al., "Pollen allergens: development and function", Sex Plant Report 9:318–323 (1996).
Li, Z–C et al., Planta 191:349–356 (1993).
McQueen–Mason et al., "Disruption of hydrogen bonding between plant cell wall polymers by proteins that induce wall extension", Proc. Natl. Acad. Sci. USA, 9:6574–6578 (1994).

(Continued)

*Primary Examiner*—Phuong T. Bui
*Assistant Examiner*—Stuart F. Baum
(74) *Attorney, Agent, or Firm*—McKee, Voorhees & Sease, P.L.C.

(57) ABSTRACT

The present invention relates to beta expansin polypeptides, nucleotide sequences encoding the same and regulatory elements and their use in altering cell wall structure in plants. Nucleic acid constructs comprising a beta expansin sequence operably linked to a promoter, or other regulatory sequence are disclosed as well as vectors, plant cells, plants, and transformed seeds containing such constructs are provided. Methods for the use of such constructs in repressing or inducing expression of a beta expansin sequences in a plant are also provided as well as methods for harvesting transgenic expansin proteins. In addition, methods are provided for inhibiting or improving cell wall structure in plants by repression or induction of expansin sequences in plants.

3 Claims, 3 Drawing Sheets

OTHER PUBLICATIONS

McQueen–Mason et al., "Expansin Mode of Action on Cell Walls", Plant Physiol. 107:87–100 (1995).

McQueen–Mason et al., Planta 190:327–331 (1993).

McQueen–Mason et al., "Two endogenous proteins that induce cell wall extension in plants", The Plant Cell 4:1425–1433 (1992).

Merriam–Webster's Collegiate Dictionary, tenth ed., pp. 1236, 1027.

Nishitani, K. and Tominaga R., J. Biol. Chem 267(29):21058–21064 (1992).

Patel, Praful, in "Biotechnology Applications and Research", eds., Cheremisinoff, P.N. and Ouellette, R.P. pp. 534–562, Technomic Publishing Company, Inc., Lancaster, PA, (1985).

Perez, et al., "cDNA cloning and immunological characterization of the rye grass allergen Loi P l", J. of Biol. Chem., vol. 265(27):16210–16215 (1990).

Padian, "Immunoglobulin fold", Encyclopedia of Immunology, Academic Press, Harcourt Brace Jovahovich, Publishers, pp. 827–833.

Proteins to Order *News of the Week*, "Program determins amino acid sequence from three–dimensional structure data", reprinted with permission from Science, copyright 1997 AAAS.

Raha, et al., "Prediction of amino acid sequence from structure", Protein Science, 9:106–119 (2000).

Scopes, R.K., Chapter 3, Protein Purification, Principles and Practice, $2^{nd}$ Ed., pp. 41–54, Springer–Verlag, New York (1987).

Shcherban, T.Y. et al., "Molecular cloning and sequence analysis of expansins—a highly conserved, multigene family of proteins that mediate cell wall extension in plants", Proc. Nat. Acad. Sci USA 92:9245–9249 (1995).

Sinnott, Botany Principles and Problems, $2^{nd}$ Ed., fifth impression, McGraww–Hil Book Co., Inc., New York and London 1929, p. 417 "The Spermatophyta".

Skolnick, et al., TISTECH, vol. 18 pp. 34–39 (2000).

Smith, et al., MMolecular Characterization of Group I Allergens of Grass Pollen, Pollen Biot. Chapter 7, pp. 124–143.

Staff, et al., "Cellular Localization of Water Soluble, Allergenic Proteins in Rye–Grass (Lolium perenne) Pollen using monoclonal and Specific IgE antibodies with immunogold probes", Histochemical J., vol. 22:276–290 (1990).

Taiz, L., "Expansins: proteins that promote cell wall loosening in plants", Proc. Natl. Acad. Sci. USA 91:7387–7389 (1994).

Taiz, L., Ann. Rev. Plant Physiol. 35:585–657 (1984).

Wu, et al., "Growth maintenance of the maize primary root at low water potentials involves increases in cell–wall extension properties, expansin activity, and wall susceptibility to expansins", Plant Physiol. 111:765–772 (1996).

Wu, et al., "Analysis and expression of the α–expansin and β–expansin gene families in maize", Plant Physiol., 126:222–232 (2001).

NCBI database for nucleotide sequences, National Center for Biotechnology Information, National Library of Medicine, NIH (Bethesda, MD, USA) Cosgrove, D.J. et al., Accession No. AF261272. May 31, 2000. 52.1% identical to SEQ ID No:1.

Wu, Y, Analysis and expression of the alpha–expansin and beta–expansin gene families in maize. Plant Physiology, 2001, vol. 126, pp. 222–232.

Lee, D–K. Expression of an expansin gene is correlated with root elongation in soybean, Plant Physiology, Mar. 2003, vol. 131, pp. 985–997.

Civello et al. (1999, Plant Physiol. 121:1273–1279) teach the cloning of an expansin gene expressed in ripening strawberry fruit.

* cited by examiner

Zm-ExpB2 cDNA nucleotide sequence (1273 nt):

AATCTGAGAGAGAGAGGGGAAAGGGCGAAGGAGGCGCAGGCAGGCATGGGCTCCCCTTCCTCCCTCCCCGCCGCGGCGGC
GCTCGTGCTCCTGGCCCTGCTCGCCGGAGCCCAGTGCCGCGAGGCCCAGTTCGACGCCGCGGACGCCGGCGCGGAGAACT
TCAACACCAGCGAGGCCGCCGTGTACTGGGGCCCCTGGCAGAAGGCCCGGGCCACCTGGTACGGCCAGCCCAACGGCGCC
GGCCCGGACGACAACGGTGGTGCGTGCGCCTTCAAGCACACCAACCAGTACCCCTTCATGTCCATGGGCTCCTGCGGAAA
CCAGCCATTGTTCAAGGACGGCAAGGGATGCGGCTCCTGCTACAAGATTCGGTGCAGGAAGGACCCGTCCTGCTCCGGGC
GGACGGAGACGGTGATCATCACCGACATGAACTACTACCCGGTGTCCAAGTACCACTTCGACCTCAGCGGCACGGCGTTC
GGCAGGCTGGCCAAGTCCGGCCTCAACGACAAGCTCCGCCACTCGGGCATCATCGACATCGAGTTCACCAGGGTGCCGTG
CGAGTTCCCTGGCCTCAAGATCGGGTTCCACGTGGAGGAGTACTCGAGCCCCGTCTACTTCGCGGTGCTGGTGGAGTACG
AGGACGGCGACGGCGACGTGGTGCAGGTGGACCTGATGGAGTCCAAGACGGCGCGCGGGCCGCCGACGGGGCGCTGGGCG
CCGATGCGCGAGTCCTGGGGCTCCGTCTGGCGCATGGACACCAACCACCGCATGCAGCCGCCCTTCTCCATCCGCATCCG
CAACGAGTCCGGCAAGACGCTCGTCGCCAGGAACGTCATCCCGGCCAACTGGAGGCCCAACACCTTCTACCGCTCCTTCG
TCCAGTACAGCTAGCTAGCTAGCTGGTTTGCGCCCCTAGTTCACCACCCACCACTACTACCACCGCCACCCACTAGACTA
CTGCTTCTGCTACCAAATACTACGGCGGAACGGAACGGCTGGTTGCCGCCGCCGCCGTCGTCCTTGGAAAGGTTGAGGCG
TCTCTTGGTCATCCGTATCGTTACCGTTGTCATGGTCCTTTGAGTCGTTGCAACCCTGATTGCAAGCCGGCAAGGGGGAA
AAAACCAACAAAGCCGTGTGGGAAAATGGAGGAGGCAGGCGTACAATGTACGCTCTCCCGCCCACTGTTGCTTTATAATC
TCTATATCATCATCATCTTCTTCTTCTCCATTCCGATCGGTGATTAATCGAAAAGTATATTGTAATGTAAAAA

*Fig. 2*

Zm-ExpB2 protein, predicted from the open reading frame begin at nt#46:

MGSPSSLPAAAALVLLALLAGAQCREAQFDAADAGAENFNTSEAAVYWGPWQKARATWYGQPNGAGPDDNGGACGFKHTNQYPFMS
MGSCGNQPLFKDGKGCGSCYKIRCRKDPSCSGRTETVIITDMNYYPVSKYHFDLSGTAFGRLAKSGLNDKLRHSGIIDIEFTRVPC
EFPGLKIGFHVEEYSSPVYFAVLVEYEDGDGDVVQVDLMESKTARGPPTGRWAPMRESWGSVWRMDTNHRMQPPFSIRIRNESGKT
LVARNVIPANWRPNTFYRSFVQYS

*Fig. 3*

ExpB4 cDNA nucleotide sequence (1273 nt):

GGCACGAGGAACAATCGAGCTACTAATAAGGTCGTATACATATCTTCTATATACTCCTCTGAAAGTTGTGAACTCCGGTC
GAGCTTAAAAACAGCAGCAATGGCGAAGCTTTGGACATTGCTGCTGGCTGCAGTGGTGGTCCTCTCACTCCTAGTGAGCC
CCATTGCTTGCACCCGAAAGCTCAACAAACCCAAGCCGAAGCCGGGCAGCTACAGGCGGCCGGTCAAGCCGAAGCCAAAA
CCGGTCACGGGCAGCTACAAGCCGGCGCCTGTGGCCGCCAGAAGAAACCACACAGCTACACCCACGCCATCGCCGACTGT
CTACGGCCCCGGTGGCTGGCTGTCAGGCGCCGGCGCCACGTACTACGGCGCGACCAACGGCGACGGGAGCGACGGCGGCG
CGTGCGGCTACCAGACGGCCGTCGGAAAGAAGCCATTCGACTCGATGATCGCCGCCGGGAGCACGCCACTGTACAGGGGA
GGCGAGGGCTGCGGCGCCTGCTACGAGGTGAAATGCACGACCAACGCCGCGTGCTCCGGCCAGCCCGTGACCATCGTAAT
CACCGACCAGTCCCCTGGCGGGCTGTTCCCCGGCGAGGTCGAGCACTTTGACATGAGCGGCACCGCCATGGGCGCCATGG
CCCGGCCCGGCATGGCCGACAAGCTCCGCGCTGGCGGCGTGCTCAGGATCCTGTACAGGAGGGTGCCGTGCAAGTACACC
GGCGTCAACATCGCGTTCAAGGTGGATCAGGGCGCGAACCCGTACTACTTCGACGTGCTCATCGAGTTCGAGGACGACGA
CGGCGACCTCAGCGCCGTGGACCTCATGGAGGCCGGCAGCGGCGTCTGGACTCCTATGGCGCACAACTGGGGCGCCACGT
GGCGCCTCAACAACGGCAGGAAGCTCAAAGCGCCGTTCGGGCTCCGGCTCACCTCCGACTCCCGCAGGGTGCTCGTCGCC
AACAACGCCATCCCGGCCGCGTGGAAGCCCGGCAAGACCTACCGCTCCTTGGTCAACTACCCTGAAAAGAGAAATACCG
ACAAGTGGATGGCGTGTATTGTGCGTCCGGGTGTTGCGAGTGGCGGCGGTGTACTACTGGTGTCGGAAAACAGAAGAGAA
TGAAAGAGGAGGTTGAAGAAGAGAATAATGTCCTTCTTCCCTCCCTGGACGGTCTCTGCAGTCCCCAAAAGTGATGTGTG
ACGGTGTTAGTCAAATCATGCCGGTAATTTGATACTTCATCTCGATTTGAGTTTTAAAAAAAAAAAAAAAAAA

*Fig. 4*

ExpB4 protein sequence, predicted from the open reading frame starting at nt# 100:

MAKLWTLLLAAVVVLSLLVSPIACTRKLNKPKPKPGSYRRPVKPKPKPVTGSYKPAPVAARRNHTATPTPSPTVYGPGGWLSGAGATYY
GATNGDGSDGGACGYQTAVGKKPFDSMIAAGSTPLYRGGEGCGACYEVKCTTNAACSGQPVTIVITDQSPGGLFPGEVEHFDMSGTAMG
AMARPGMADKLRAGGVLRILYRRVPCKYTGVNIAFKVDQGANPYYFDVLIEFEDDDGDLSAVDLMEAGSGVWTPMAHNWGATWRLNNGR
KLKAPFGLRLTSDSRRVLVANNAIPAAWKPGKTYRSLVNYP

*Fig. 5*

SEQUENCE LISTING

```
<160> NUMBER OF SEQ ID NOS: 22

<210> SEQ ID NO 1
<211> LENGTH: 1273
<212> TYPE: DNA
<213> ORGANISM: Zea mays
<220> FEATURE:
<221> NAME/KEY: CDS
<222> LOCATION: (46)..(894)
<223> OTHER INFORMATION:

<400> SEQUENCE: 1
aatctgagag agagagggga aagggcgaag gaggcgcagg caggc atg ggc tcc cct      57
                                                 Met Gly Ser Pro
                                                  1 tcc tcc ctc ccc gcc gcg gcg gcg ctc gtg ctc ctg gcc ctg ctc gcc     105
Ser Ser Leu Pro Ala Ala Ala Ala Leu Val Leu Leu Ala Leu Leu Ala
 5              10                  15                  20 gga gcc cag tgc cgc gag gcc cag ttc gac gcc gcg gac gcc ggc gcg     153
Gly Ala Gln Cys Arg Glu Ala Gln Phe Asp Ala Ala Asp Ala Gly Ala
                 25                  30                  35 gag aac ttc aac acc agc gag gcc gcc gtg tac tgg ggc ccc tgg cag     201
Glu Asn Phe Asn Thr Ser Glu Ala Ala Val Tyr Trp Gly Pro Trp Gln
```

```
               40                  45                  50
aag gcc cgg gcc acc tgg tac ggc cag ccc aac ggc gcc ggc ccg gac       249
Lys Ala Arg Ala Thr Trp Tyr Gly Gln Pro Asn Gly Ala Gly Pro Asp
         55                  60                  65 gac aac ggt ggt gcg tgc ggc ttc aag cac acc aac cag tac ccc ttc       297
Asp Asn Gly Gly Ala Cys Gly Phe Lys His Thr Asn Gln Tyr Pro Phe
 70                  75                  80 atg tcc atg ggc tcc tgc gga aac cag cca ttg ttc aag gac ggc aag       345
Met Ser Met Gly Ser Cys Gly Asn Gln Pro Leu Phe Lys Asp Gly Lys
 85                  90                  95                 100 gga tgc ggc tcc tgc tac aag att cgg tgc agg aag gac ccg tcc tgc       393
Gly Cys Gly Ser Cys Tyr Lys Ile Arg Cys Arg Lys Asp Pro Ser Cys
                105                 110                 115 tcc ggg cgg acg gag acg gtg atc atc acc gac atg aac tac tac ccg       441
Ser Gly Arg Thr Glu Thr Val Ile Ile Thr Asp Met Asn Tyr Tyr Pro
            120                 125                 130 gtg tcc aag tac cac ttc gac ctc agc ggc acg gcg ttc ggc agg ctg       489
Val Ser Lys Tyr His Phe Asp Leu Ser Gly Thr Ala Phe Gly Arg Leu
        135                 140                 145 gcc aag tcc ggc ctc aac gac aag ctc cgc cac tcg ggc atc atc gac       537
Ala Lys Ser Gly Leu Asn Asp Lys Leu Arg His Ser Gly Ile Ile Asp
    150                 155                 160 atc gag ttc acc agg gtg ccg tgc gag ttc cct ggc ctc aag atc ggg       585
Ile Glu Phe Thr Arg Val Pro Cys Glu Phe Pro Gly Leu Lys Ile Gly
165                 170                 175                 180 ttc cac gtg gag gag tac tcg agc ccc gtc tac ttc gcg gtg ctg gtg       633
Phe His Val Glu Glu Tyr Ser Ser Pro Val Tyr Phe Ala Val Leu Val
                185                 190                 195 gag tac gag gac ggc gac ggc gac gtg gtg cag gtg gac ctg atg gag       681
Glu Tyr Glu Asp Gly Asp Gly Asp Val Val Gln Val Asp Leu Met Glu
            200                 205                 210 tcc aag acg gcg cgc ggg ccg ccg acg ggg cgc tgg gcg ccg atg cgc       729
Ser Lys Thr Ala Arg Gly Pro Pro Thr Gly Arg Trp Ala Pro Met Arg
        215                 220                 225 gag tcc tgg ggc tcc gtc tgg cgc atg gac acc aac cac cgc atg cag       777
Glu Ser Trp Gly Ser Val Trp Arg Met Asp Thr Asn His Arg Met Gln
    230                 235                 240 ccg ccc ttc tcc atc cgc atc cgc aac gag tcc ggc aag acg ctc gtc       825
Pro Pro Phe Ser Ile Arg Ile Arg Asn Glu Ser Gly Lys Thr Leu Val
245                 250                 255                 260 gcc agg aac gtc atc ccg gcc aac tgg agg ccc aac acc ttc tac cgc       873
Ala Arg Asn Val Ile Pro Ala Asn Trp Arg Pro Asn Thr Phe Tyr Arg
                265                 270                 275 tcc ttc gtc cag tac agc tag ctagctagct ggtttgcgcc cctagttcac         924
Ser Phe Val Gln Tyr Ser
            280 cacccaccac tactaccacc gccacccact agactactgc ttctgctacc aaatactacg    984 gcggaacgga acggctggtt gccgccgccg ccgtcgtcct tggaaaggtt gaggcgtctc   1044 ttggtcatcc gtatcgttac cgttgtcatg gtcctttgag tcgttgcaac cctgattgca   1104 agccggcaag ggggaaaaaa ccaacaaagc cgtgtgggaa aatggaggag gcaggcgtac   1164 aatgtacgct ctcccgccca ctgttgcttt ataatctcta tatcatcatc atcttcttct   1224 tctccattcc gatcggtgat taatcgaaaa gtatattgta atgtaaaaa              1273

<210> SEQ ID NO 2
<211> LENGTH: 282
<212> TYPE: PRT
<213> ORGANISM: Zea mays
```

```
<400> SEQUENCE: 2

Met Gly Ser Pro Ser Ser Leu Pro Ala Ala Ala Ala Leu Val Leu Leu
1               5                   10                  15

Ala Leu Leu Ala Gly Ala Gln Cys Arg Glu Ala Gln Phe Asp Ala Ala
            20                  25                  30

Asp Ala Gly Ala Glu Asn Phe Asn Thr Ser Glu Ala Ala Val Tyr Trp
        35                  40                  45

Gly Pro Trp Gln Lys Ala Arg Ala Thr Trp Tyr Gly Gln Pro Asn Gly
    50                  55                  60

Ala Gly Pro Asp Asp Asn Gly Gly Ala Cys Gly Phe Lys His Thr Asn
65                  70                  75                  80

Gln Tyr Pro Phe Met Ser Met Gly Ser Cys Gly Asn Gln Pro Leu Phe
                85                  90                  95

Lys Asp Gly Lys Gly Cys Gly Ser Cys Tyr Lys Ile Arg Cys Arg Lys
            100                 105                 110

Asp Pro Ser Cys Ser Gly Arg Thr Glu Thr Val Ile Ile Thr Asp Met
        115                 120                 125

Asn Tyr Tyr Pro Val Ser Lys Tyr His Phe Asp Leu Ser Gly Thr Ala
    130                 135                 140

Phe Gly Arg Leu Ala Lys Ser Gly Leu Asn Asp Lys Leu Arg His Ser
145                 150                 155                 160

Gly Ile Ile Asp Ile Glu Phe Thr Arg Val Pro Cys Glu Phe Pro Gly
                165                 170                 175

Leu Lys Ile Gly Phe His Val Glu Glu Tyr Ser Ser Pro Val Tyr Phe
            180                 185                 190

Ala Val Leu Val Glu Tyr Glu Asp Gly Asp Gly Asp Val Val Gln Val
        195                 200                 205

Asp Leu Met Glu Ser Lys Thr Ala Arg Gly Pro Pro Thr Gly Arg Trp
    210                 215                 220

Ala Pro Met Arg Glu Ser Trp Gly Ser Val Trp Arg Met Asp Thr Asn
225                 230                 235                 240

His Arg Met Gln Pro Pro Phe Ser Ile Arg Ile Arg Asn Glu Ser Gly
                245                 250                 255

Lys Thr Leu Val Ala Arg Asn Val Ile Pro Ala Asn Trp Arg Pro Asn
            260                 265                 270

Thr Phe Tyr Arg Ser Phe Val Gln Tyr Ser
        275                 280

<210> SEQ ID NO 3
<211> LENGTH: 1273
<212> TYPE: DNA
<213> ORGANISM: Zea mays
<220> FEATURE:
<221> NAME/KEY: CDS
<222> LOCATION: (100)..(1026)
<223> OTHER INFORMATION:

<400> SEQUENCE: 3
ggcacgagga acaatcgagc tactaataag gtcgtataca tatcttctat atactcctct    60
gaaagttgtg aactccggtc gagcttaaaa acagcagca atg gcg aag ctt tgg     114
                                            Met Ala Lys Leu Trp
                                              1               5 aca ttg ctg ctg gct gca gtg gtg gtc ctc tca ctc cta gtg agc ccc    162
Thr Leu Leu Leu Ala Ala Val Val Val Leu Ser Leu Leu Val Ser Pro
            10                  15                  20
```

-continued

| | | |
|---|---|---|
| att gct tgc acc cga aag ctc aac aaa ccc aag ccg aag ccg ggc agc<br>Ile Ala Cys Thr Arg Lys Leu Asn Lys Pro Lys Pro Lys Pro Gly Ser<br>                   25                       30                    35 | 210 |
| tac agg cgg ccg gtc aag ccg aag cca aaa ccg gtc acg ggc agc tac<br>Tyr Arg Arg Pro Val Lys Pro Lys Pro Lys Pro Val Thr Gly Ser Tyr<br>        40                       45                       50 | 258 |
| aag ccg gcg cct gtg gcc gcc aga aga aac cac aca gct aca ccc acg<br>Lys Pro Ala Pro Val Ala Ala Arg Arg Asn His Thr Ala Thr Pro Thr<br>55                       60                       65 | 306 |
| cca tcg ccg act gtc tac ggc ccc ggt ggc tgg ctg tca ggc gcc ggc<br>Pro Ser Pro Thr Val Tyr Gly Pro Gly Gly Trp Leu Ser Gly Ala Gly<br>70                       75                   80                   85 | 354 |
| gcc acg tac tac ggc gcg acc aac ggc gac ggg agc gac ggc ggc gcg<br>Ala Thr Tyr Tyr Gly Ala Thr Asn Gly Asp Gly Ser Asp Gly Gly Ala<br>                     90                       95                   100 | 402 |
| tgc ggc tac cag acg gcc gtc gga aag aag cca ttc gac tcg atg atc<br>Cys Gly Tyr Gln Thr Ala Val Gly Lys Lys Pro Phe Asp Ser Met Ile<br>                 105                     110                   115 | 450 |
| gcc gcc ggg agc acg cca ctg tac agg gga ggc gag ggc tgc ggc gcc<br>Ala Ala Gly Ser Thr Pro Leu Tyr Arg Gly Gly Glu Gly Cys Gly Ala<br>             120                     125                   130 | 498 |
| tgc tac gag gtg aaa tgc acg acc aac gcc gcg tgc tcc ggc cag ccc<br>Cys Tyr Glu Val Lys Cys Thr Thr Asn Ala Ala Cys Ser Gly Gln Pro<br>135                       140                     145 | 546 |
| gtg acc atc gta atc acc gac cag tcc cct ggc ggg ctg ttc ccc ggc<br>Val Thr Ile Val Ile Thr Asp Gln Ser Pro Gly Gly Leu Phe Pro Gly<br>150                       155                     160                 165 | 594 |
| gag gtc gag cac ttt gac atg agc ggc acc gcc atg ggc gcc atg gcc<br>Glu Val Glu His Phe Asp Met Ser Gly Thr Ala Met Gly Ala Met Ala<br>                   170                     175                   180 | 642 |
| cgg ccc ggc atg gcc gac aag ctc cgc gct ggc ggc gtg ctc agg atc<br>Arg Pro Gly Met Ala Asp Lys Leu Arg Ala Gly Gly Val Leu Arg Ile<br>             185                     190                   195 | 690 |
| ctg tac agg agg gtg ccg tgc aag tac acc ggc gtc aac atc gcg ttc<br>Leu Tyr Arg Arg Val Pro Cys Lys Tyr Thr Gly Val Asn Ile Ala Phe<br>             200                     205                   210 | 738 |
| aag gtg gat cag ggc gcg aac ccg tac tac ttc gac gtg ctc atc gag<br>Lys Val Asp Gln Gly Ala Asn Pro Tyr Tyr Phe Asp Val Leu Ile Glu<br>215                       220                     225 | 786 |
| ttc gag gac gac gac ggc gac ctc agc gcc gtg gac ctc atg gag gcc<br>Phe Glu Asp Asp Asp Gly Asp Leu Ser Ala Val Asp Leu Met Glu Ala<br>230                       235                     240                 245 | 834 |
| ggc agc ggc gtc tgg act cct atg gcg cac aac tgg ggc gcc acg tgg<br>Gly Ser Gly Val Trp Thr Pro Met Ala His Asn Trp Gly Ala Thr Trp<br>                   250                     255                   260 | 882 |
| cgc ctc aac aac ggc agg aag ctc aaa gcg ccg ttc ggg ctc cgg ctc<br>Arg Leu Asn Asn Gly Arg Lys Leu Lys Ala Pro Phe Gly Leu Arg Leu<br>             265                     270                   275 | 930 |
| acc tcc gac tcc cgc agg gtg ctc gtc gcc aac aac gcc atc ccg gcc<br>Thr Ser Asp Ser Arg Arg Val Leu Val Ala Asn Asn Ala Ile Pro Ala<br>280                       285                     290 | 978 |
| gcg tgg aag ccc ggc aag acc tac cgc tcc ttg gtc aac tac ccc tga<br>Ala Trp Lys Pro Gly Lys Thr Tyr Arg Ser Leu Val Asn Tyr Pro<br>             295                     300                   305 | 1026 |
| aaagagaaat accgacaagt ggatggcgtg tattgtgcgt ccgggtgttg cgagtggcgg | 1086 |
| cggtgtacta ctggtgtcgg aaaacagaag agaatgaaag aggaggttga agaagagaat | 1146 |
| aatgtccttc ttccctccct ggacggtctc tgcagtcccc aaaagtgatg tgtgacggtg | 1206 |
| ttagtcaaat catgccggta atttgatact tcatctcgat ttgagtttta aaaaaaaaaa | 1266 | aaaaaaa                                                                1273

<210> SEQ ID NO 4
<211> LENGTH: 308
<212> TYPE: PRT
<213> ORGANISM: Zea mays

<400> SEQUENCE: 4

Met Ala Lys Leu Trp Thr Leu Leu Ala Val Val Leu Ser
1               5                   10              15

Leu Leu Val Ser Pro Ile Ala Cys Thr Arg Lys Leu Asn Lys Pro Lys
            20                  25                  30

Pro Lys Pro Gly Ser Tyr Arg Arg Pro Val Lys Pro Lys Pro
        35                  40                  45

Val Thr Gly Ser Tyr Lys Pro Ala Pro Val Ala Ala Arg Arg Asn His
    50                  55                  60

Thr Ala Thr Pro Thr Pro Ser Pro Thr Val Tyr Gly Pro Gly Gly Trp
65                  70                  75                  80

Leu Ser Gly Ala Gly Ala Thr Tyr Tyr Gly Ala Thr Asn Gly Asp Gly
                85                  90                  95

Ser Asp Gly Gly Ala Cys Gly Tyr Gln Thr Ala Val Gly Lys Lys Pro
            100                 105                 110

Phe Asp Ser Met Ile Ala Ala Gly Ser Thr Pro Leu Tyr Arg Gly Gly
        115                 120                 125

Glu Gly Cys Gly Ala Cys Tyr Glu Val Lys Cys Thr Thr Asn Ala Ala
    130                 135                 140

Cys Ser Gly Gln Pro Val Thr Ile Val Ile Thr Asp Gln Ser Pro Gly
145                 150                 155                 160

Gly Leu Phe Pro Gly Glu Val Glu His Phe Asp Met Ser Gly Thr Ala
                165                 170                 175

Met Gly Ala Met Ala Arg Pro Gly Met Ala Asp Lys Leu Arg Ala Gly
            180                 185                 190

Gly Val Leu Arg Ile Leu Tyr Arg Arg Val Pro Cys Lys Tyr Thr Gly
        195                 200                 205

Val Asn Ile Ala Phe Lys Val Asp Gln Gly Ala Asn Pro Tyr Tyr Phe
    210                 215                 220

Asp Val Leu Ile Glu Phe Glu Asp Asp Gly Asp Leu Ser Ala Val
225                 230                 235                 240

Asp Leu Met Glu Ala Gly Ser Gly Val Trp Thr Pro Met Ala His Asn
                245                 250                 255

Trp Gly Ala Thr Trp Arg Leu Asn Asn Gly Arg Lys Leu Lys Ala Pro
            260                 265                 270

Phe Gly Leu Arg Leu Thr Ser Asp Ser Arg Arg Val Leu Val Ala Asn
        275                 280                 285

Asn Ala Ile Pro Ala Ala Trp Lys Pro Gly Lys Thr Tyr Arg Ser Leu
    290                 295                 300

Val Asn Tyr Pro
305

<210> SEQ ID NO 5
<211> LENGTH: 18
<212> TYPE: DNA
<213> ORGANISM: Zea mays

<400> SEQUENCE: 5

```
agctagctgg tttgcgcc                                              18

<210> SEQ ID NO 6
<211> LENGTH: 17
<212> TYPE: DNA
<213> ORGANISM: Zea mays

<400> SEQUENCE: 6
aagcaacagt gggcggg                                               17

<210> SEQ ID NO 7
<211> LENGTH: 19
<212> TYPE: DNA
<213> ORGANISM: Zea mays

<400> SEQUENCE: 7
cctgaaaaga gaaataccg                                             19

<210> SEQ ID NO 8
<211> LENGTH: 19
<212> TYPE: DNA
<213> ORGANISM: Zea mays

<400> SEQUENCE: 8
gtatcaaatt accggcatg                                             19

<210> SEQ ID NO 9
<211> LENGTH: 5
<212> TYPE: PRT
<213> ORGANISM: Artificial sequence
<220> FEATURE:
<223> OTHER INFORMATION: Conserved expansin sequence
<220> FEATURE:
<221> NAME/KEY: misc_feature
<222> LOCATION: (3)..(3)
<223> OTHER INFORMATION: Xaa can be Phe or Trp

<400> SEQUENCE: 9

Ala Thr Xaa Tyr Gly
1               5

<210> SEQ ID NO 10
<211> LENGTH: 5
<212> TYPE: PRT
<213> ORGANISM: Artificial sequence
<220> FEATURE:
<223> OTHER INFORMATION: Conserved expansin sequence

<400> SEQUENCE: 10

Gly Gly Ala Cys Gly
1               5

<210> SEQ ID NO 11
<211> LENGTH: 231
<212> TYPE: PRT
<213> ORGANISM: Artificial sequence
<220> FEATURE:
<223> OTHER INFORMATION: Consensus sequence from BLAST comparison

<400> SEQUENCE: 11

Cys Ala Phe Ala Asp Ala Ala Phe Asn Ser Ala Val Tyr Trp Gly
1               5                   10                  15

Pro Trp Lys Ala Arg Ala Thr Trp Tyr Gly Gln Pro Asn Gly Ala Gly
                20                  25                  30

Pro Asp Asp Asn Gly Gly Ala Cys Gly Phe Lys His Thr Asn Gln Tyr
```

-continued

```
                35                  40                  45
Pro Phe Met Ser Met Ser Cys Gly Asn Gln Pro Leu Phe Lys Asp Gly
             50                  55                  60

Lys Gly Cys Gly Ser Cys Tyr Lys Ile Arg Cys Lys Asp Ser Cys Ser
 65                  70                  75                  80

Gly Arg Glu Thr Val Ile Ile Thr Asp Met Asn Tyr Tyr Pro Val His
                 85                  90                  95

Phe Asp Leu Ser Gly Thr Ala Phe Gly Arg Leu Ala Lys Gly Leu Asn
                100                 105                 110

Asp Lys Leu Arg His Ser Gly Ile Ile Asp Ile Glu Phe Thr Arg Val
            115                 120                 125

Pro Cys Glu Phe Pro Gly Leu Lys Ile Gly Phe His Val Glu Glu Tyr
        130                 135                 140

Ser Pro Val Tyr Phe Ala Val Leu Val Glu Tyr Glu Asp Gly Asp Gly
145                 150                 155                 160

Asp Val Val Gln Val Asp Leu Met Glu Ser Lys Thr Ala Gly Pro Pro
                165                 170                 175

Thr Gly Trp Pro Met Arg Glu Ser Trp Gly Ser Trp Arg Asp Thr Asn
            180                 185                 190

His Arg Gln Pro Phe Ser Ile Arg Ile Arg Asn Glu Ser Gly Lys Thr
        195                 200                 205

Leu Val Ala Asn Val Ile Pro Ala Asn Trp Arg Pro Asn Thr Phe Tyr
    210                 215                 220

Arg Ser Phe Val Gln Tyr Ser
225                 230

<210> SEQ ID NO 12
<211> LENGTH: 265
<212> TYPE: PRT
<213> ORGANISM: Oryza sativa

<400> SEQUENCE: 12

Cys Ala Ala Ala Asp Phe Asn Ala Thr Asp Ala Asp Ala Asp Phe Ala
  1               5                  10                  15

Gly Asn Gly Trp Asp Phe Asn Ser Ser Asp Ala Ala Val Tyr Trp Gly
                 20                  25                  30

Pro Trp Thr Lys Ala Arg Ala Thr Trp Tyr Gly Gln Pro Asn Gly Ala
             35                  40                  45

Gly Pro Asp Asp Asn Gly Gly Ala Cys Gly Phe Lys His Thr Asn Gln
         50                  55                  60

Tyr Pro Phe Met Ser Met Thr Ser Cys Gly Asn Gln Pro Leu Phe Lys
 65                  70                  75                  80

Asp Gly Lys Gly Cys Gly Ser Cys Tyr Lys Ile Arg Cys Thr Lys Asp
                 85                  90                  95

Gln Ser Cys Ser Gly Arg Ser Glu Thr Val Ile Ile Thr Asp Met Asn
            100                 105                 110

Tyr Tyr Pro Val Ala Pro Phe His Phe Asp Leu Ser Gly Thr Ala Phe
        115                 120                 125

Gly Arg Leu Ala Lys Pro Gly Leu Asn Asp Lys Leu Arg His Ser Gly
    130                 135                 140

Ile Ile Asp Ile Glu Phe Thr Arg Val Pro Cys Glu Phe Pro Gly Leu
145                 150                 155                 160

Lys Ile Gly Phe His Val Glu Glu Tyr Ser Asn Pro Val Tyr Phe Ala
                165                 170                 175
```

```
Val Leu Val Glu Tyr Glu Asp Gly Asp Gly Asp Val Val Gln Val Asp
            180                 185                 190

Leu Met Glu Ser Lys Thr Ala His Gly Pro Pro Thr Gly Lys Trp Thr
        195                 200                 205

Pro Met Arg Glu Ser Trp Gly Ser Ile Trp Arg Leu Asp Thr Asn His
    210                 215                 220

Arg Leu Gln Ala Pro Phe Ser Ile Arg Ile Arg Asn Glu Ser Gly Lys
225                 230                 235                 240

Thr Leu Val Ala Asn Asn Val Ile Pro Ala Asn Trp Arg Pro Asn Thr
                245                 250                 255

Phe Tyr Arg Ser Phe Val Gln Tyr Ser
            260                 265

<210> SEQ ID NO 13
<211> LENGTH: 190
<212> TYPE: PRT
<213> ORGANISM: Artificial sequence
<220> FEATURE:
<223> OTHER INFORMATION: Consensus sequence from BLAST comparison

<400> SEQUENCE: 13

Asn Asn Ser Ala Tyr Trp Ala Arg Ala Thr Trp Tyr Gly Pro Gly Ala
1               5                   10                  15

Gly Pro Asp Asp Asn Gly Gly Ala Cys Gly Phe Lys Asn Gln Tyr Pro
            20                  25                  30

Phe Ser Met Ser Cys Gly Asn Pro Phe Lys Asp Gly Lys Gly Cys Gly
        35                  40                  45

Ser Cys Tyr Ile Arg Cys Lys Asp Pro Ser Cys Ser Gly Glu Thr Val
    50                  55                  60

Ile Ile Thr Asp Met Asn Tyr Tyr Pro Val Tyr His Phe Asp Leu Ser
65                  70                  75                  80

Gly Thr Ala Phe Gly Ala Lys Gly Leu Asn Asp Lys Leu Arg His Ser
            85                  90                  95

Gly Ile Ile Asp Ile Phe Arg Val Pro Cys Pro Gly Leu Lys Ile Phe
            100                 105                 110

His Val Glu Glu Ser Pro Val Tyr Phe Ala Val Leu Val Glu Tyr Glu
        115                 120                 125

Asp Asp Gly Asp Val Val Gln Val Asp Leu Met Glu Ser Lys Ala Gly
    130                 135                 140

Thr Gly Trp Pro Met Arg Glu Ser Trp Gly Ser Trp Arg Asp Asn His
145                 150                 155                 160

Arg Gln Pro Phe Ser Arg Ile Arg Ser Gly Lys Thr Leu Val Ala Asn
                165                 170                 175

Val Ile Pro Ala Asn Trp Pro Asn Tyr Arg Ser Val Gln Ser
            180                 185                 190

<210> SEQ ID NO 14
<211> LENGTH: 245
<212> TYPE: PRT
<213> ORGANISM: Oryza sativa

<400> SEQUENCE: 14

Asn Tyr Asn Val Ser Asp Ala Ser Ala Tyr Gly Ser Gly Trp Leu Pro
1               5                   10                  15

Ala Arg Ala Thr Trp Tyr Gly Ala Pro Thr Gly Ala Gly Pro Asp Asp
            20                  25                  30

Asn Gly Gly Ala Cys Gly Phe Lys Asn Val Asn Gln Tyr Pro Phe Ser
```

```
                35                  40                  45
Ser Met Thr Ser Cys Gly Asn Glu Pro Ile Phe Lys Asp Gly Lys Gly
     50                  55                  60

Cys Gly Ser Cys Tyr Gln Ile Arg Cys Asn Lys Asp Pro Ser Cys Ser
 65                  70                  75                  80

Gly Asn Ile Glu Thr Val Ile Ile Thr Asp Met Asn Tyr Tyr Pro Val
                 85                  90                  95

Ala Arg Tyr His Phe Asp Leu Ser Gly Thr Ala Phe Gly Ala Met Ala
            100                 105                 110

Lys Pro Gly Leu Asn Asp Lys Leu Arg His Ser Gly Ile Ile Asp Ile
            115                 120                 125

Gln Phe Arg Arg Val Pro Cys Asn Tyr Pro Gly Leu Lys Ile Asn Phe
130                 135                 140

His Val Glu Glu Gly Ser Asn Pro Val Tyr Phe Ala Val Leu Val Glu
145                 150                 155                 160

Tyr Glu Asp Leu Asp Gly Asp Val Val Gln Val Asp Leu Met Glu Ser
                165                 170                 175

Lys Ser Ala Tyr Gly Gly Ala Thr Gly Val Trp Thr Pro Met Arg Glu
            180                 185                 190

Ser Trp Gly Ser Ile Trp Arg Leu Asp Ser Asn His Arg Leu Gln Ala
            195                 200                 205

Pro Phe Ser Leu Arg Ile Arg Ser Asp Ser Gly Lys Thr Leu Val Ala
210                 215                 220

Asn Asn Val Ile Pro Ala Asn Trp Ser Pro Asn Ser Asn Tyr Arg Ser
225                 230                 235                 240

Ile Val Gln Phe Ser
            245

<210> SEQ ID NO 15
<211> LENGTH: 735
<212> TYPE: DNA
<213> ORGANISM: Oryza sativa

<400> SEQUENCE: 15
acttcaactc cagcgacgcc gccgtctact ggggcccctg gaccaaggcc agggccacct    60
ggtacggcca gcccaacggc gccggccccg acgacaacgg cggcgcgtgc gggttcaagc   120
acaccaacca gtacccgttc atgtcgatga cctcctgcgg caaccagcca ttgttcaagg   180
acggcaaggg atgcggctct tgctacaaga tcagatgcac caaggaccag tcgtgctccg   240
gcaggtcgga gacggtgatc atcaccgaca tgaactacta cccggtggct ccgttccact   300
tcgacctcag cggcacggcg ttcggcaggc tcgccaagcc tggcctcaac gacaagctgc   360
gccactccgg catcatcgac atcgagttca ccagggtgcc atgcgagttc cggggctca    420
agatcgggtt ccacgtggag gagtactcga accctgtgta cttcgcggtg ctggtggagt   480
acgaggacgg cgacggcgac gtggtgcagg tggacctgat ggagtcgaag acggcgcacg   540
ggccgccgac ggggaagtgg acgccgatga gggagtcgtg gggctccatc tggaggctgg   600
acaccaacca caggctccag gccccttct ccatccgcat ccgcaacgag tccggcaaga   660
cgctcgtcgc caacaacgtc atcccggcca actggaggcc caacacattc taccgctcct   720
cgtccagta cagct                                                    735

<210> SEQ ID NO 16
<211> LENGTH: 258
<212> TYPE: DNA
```

```
<213> ORGANISM: Oryza sativa

<400> SEQUENCE: 16
catcaccgac atgaactact tccccctctc ccagtaccac ttcgacctca gcggcatcgc      60
cttcggccgc ctcgccaagc ccggccgcgc cgacgacctc cgccgcgcgg ggatcatcga     120
cgtgcagttc gcgcgcgtgc cgtgcgagtt cccgggcctc aaggtgggat tccacgtgga     180
ggaagggtcc agccccgtgt acctggcggt gctggtggag tacgagaacg gcgacggaga     240
cgtggcgcag gtggacct                                                   258

<210> SEQ ID NO 17
<211> LENGTH: 170
<212> TYPE: DNA
<213> ORGANISM: Oryza sativa

<400> SEQUENCE: 17
cgccgatgcg ggagtcgtgg gggtcggtgt ggaggctgga ctccaaccac cgcctgcggg      60
cgccattctc catccgcatc cggagcgact ccggcaagac gttggtggca cccgacgtca     120 tcccctcaa ctggacgccc aacacctttt accgttcctt cgtccagtac                 170

<210> SEQ ID NO 18
<211> LENGTH: 147
<212> TYPE: DNA
<213> ORGANISM: Oryza sativa

<400> SEQUENCE: 18
tggtacgggc agccgaacgg cgccggggcg gcggacaacg gcgggcgtg cgggttcaag       60 aaggtgaacc agtacccgtt catggggatg acgtcgtgcg ggaaccagcc gctgtacaag     120
ggcggcaagg gctgcggctc ctgctac                                         147

<210> SEQ ID NO 19
<211> LENGTH: 138
<212> TYPE: PRT
<213> ORGANISM: Artificial sequence
<220> FEATURE:
<223> OTHER INFORMATION: Consensus sequence from BLAST comparison

<400> SEQUENCE: 19

Asn Thr Ala Gly Trp Ser Gly Asp Gly Ser Gly Ala Cys Gly Tyr
  1               5                  10                  15

Gln Ala Val Gly Pro Phe Ser Met Ile Ala Ala Gly Leu Gly Gly Cys
             20                  25                  30

Gly Cys Tyr Lys Cys Thr Asn Ala Cys Ser Gly Pro Val Thr Val Ile
         35                  40                  45

Thr Asp Pro Gly Gly Glu His Phe Asp Met Ser Gly Thr Ala Gly Ala
 50                  55                  60

Met Ala Gly Met Asp Leu Arg Gly Val Leu Ile Tyr Arg Val Pro Cys
 65                  70                  75                  80

Asn Ala Phe Lys Val Asp Gly Asn Pro Tyr Tyr Leu Asp Gly Asp Leu
                 85                  90                  95

Ala Val Met Ala Gly Gly Trp Met Trp Gly Ala Thr Trp Arg Leu Asn
                100                 105                 110

Gly Leu Pro Phe Arg Leu Thr Ser Ser Val Leu Val Ala Asn Asn Ile
            115                 120                 125

Pro Trp Gly Thr Tyr Arg Ser Val Asn Tyr
        130                 135
```

```
<210> SEQ ID NO 20
<211> LENGTH: 247
<212> TYPE: PRT
<213> ORGANISM: Oryza sativa

<400> SEQUENCE: 20

Gln Asn Tyr Thr Ala Gly Arg Arg Ser Thr Met Ser Leu Gly Arg Gly
 1               5                  10                  15

Tyr Gly Trp Ser Ser Gly Ala Thr Trp Tyr Gly Pro Gln Gly
            20                  25                  30

Asp Gly Ser Glu Gly Gly Ala Cys Gly Tyr Gln Ser Ala Val Gly Gln
            35                  40                  45

Arg Pro Phe Ser Ser Met Ile Ala Ala Gly Pro Ser Leu Phe Lys
     50                  55                  60

Asn Gly Lys Gly Cys Gly Ser Cys Tyr Gln Ile Lys Cys Thr Gly Asn
65                  70                  75                  80

Arg Ala Cys Ser Gly Arg Pro Val Thr Val Ile Thr Asp Ser Cys
                85                  90                  95

Pro Gly Gly Val Cys Leu Asn Glu Ala Ala His Phe Asp Met Ser Gly
                100                 105                 110

Thr Ala Phe Gly Ala Met Ala Asn Arg Gly Met Gly Asp Arg Leu Arg
            115                 120                 125

Ser Ala Gly Val Leu Lys Ile Gln Tyr Lys Arg Val Pro Cys Arg Phe
        130                 135                 140

Ala Met Asn Val Ala Phe Lys Val Asp Ala Gly Ser Asn Pro Tyr Tyr
145                 150                 155                 160

Leu Ala Ile Leu Val Gln Tyr Ala Asn Gly Asp Gly Asp Leu Ala Ala
                165                 170                 175

Val His Ile Met Lys Ala Arg Gly Gly Gly Trp Lys Ala Met Gln
            180                 185                 190

Gln Ser Trp Gly Ala Thr Trp Arg Leu Asn Ser Asn Thr Gly Lys Pro
        195                 200                 205

Leu Ser Pro Pro Phe Ser Ile Arg Leu Thr Ser Gly Ser Gly Lys Val
    210                 215                 220

Leu Val Ala Asn Asn Val Ile Pro Ser Gly Trp Gln Ala Gly Leu Thr
225                 230                 235                 240

Tyr Arg Ser Thr Val Asn Tyr
                245

<210> SEQ ID NO 21
<211> LENGTH: 118
<212> TYPE: PRT
<213> ORGANISM: Artificial sequence
<220> FEATURE:
<223> OTHER INFORMATION: Consensus sequence from BLAST comparison

<400> SEQUENCE: 21

Cys Lys Lys Pro Lys Pro Pro Gly Ser Ala Pro Gly Gly Gly Trp Leu
 1               5                  10                  15

Asn Gly Gly Asp Gly Gly Ala Cys Gly Val Pro Phe Met Gly Pro Leu
                20                  25                  30

Gly Gly Cys Gly Cys Tyr Cys Ala Cys Ser Gly Pro Thr Ile Thr Asp
            35                  40                  45

Pro His Phe Asp Ser Gly Thr Ala Gly Ala Met Ala Asp Leu Arg Gly
     50                  55                  60

Ile Arg Arg Val Pro Cys Tyr Gly Phe Val Gln Gly Asn Pro Tyr Leu
```

```
              65                  70                  75                  80
Glu Glu Asp Gly Asp Val Asp Leu Met Glu Gly Val Trp Thr Pro Met
                    85                  90                  95
Trp Gly Trp Arg Leu Leu Pro Phe Leu Arg Thr Ser Leu Ala Ile Pro
                100                 105                 110
Ala Trp Pro Tyr Ser Val
            115

<210> SEQ ID NO 22
<211> LENGTH: 299
<212> TYPE: PRT
<213> ORGANISM: Oryza sativa

<400> SEQUENCE: 22

Cys Ser Ala Lys His His Lys Pro Lys Pro Thr Pro Gly Gly Ile Ser
1               5                   10                  15
Gly Asn Ala Ser Ser Ser Ser Asn Ser Ser Thr Pro Ser Ile Pro
            20                  25                  30
Pro Pro Val Ala Pro Thr Pro Thr Ala Pro Thr Pro Pro Ile Pro Ser
                35                  40                  45
Pro Gly Thr Gly Ser Ser Asn Gly Ser Ser Gly Gly Gly Gly Gly
        50                  55                  60
Trp Leu Asn Ala Arg Ala Thr Trp Tyr Gly Ala Pro Asn Gly Ala Gly
65                  70                  75                  80
Pro Asp Asp Asn Gly Gly Ala Cys Gly Phe Lys Asn Val Asn Leu Pro
                85                  90                  95
Pro Phe Ser Ala Met Thr Ser Cys Gly Asn Glu Pro Leu Phe Lys Asp
                100                 105                 110
Gly Lys Gly Cys Gly Ser Cys Tyr Gln Ile Arg Cys Val Gly His Pro
            115                 120                 125
Ala Cys Ser Gly Leu Pro Glu Thr Val Ile Ile Thr Asp Met Asn Tyr
        130                 135                 140
Tyr Pro Val Ser Leu Tyr His Phe Asp Leu Ser Gly Thr Ala Phe Gly
145                 150                 155                 160
Ala Met Ala Lys Asp Asn Arg Asn Asp Glu Leu Arg His Ala Gly Ile
                165                 170                 175
Ile Asp Ile Gln Phe Arg Arg Val Pro Cys Gln Tyr Pro Gly Leu Thr
            180                 185                 190
Val Thr Phe His Val Glu Gln Gly Ser Asn Pro Val Tyr Met Ala Ile
        195                 200                 205
Leu Val Glu Tyr Glu Asn Gly Asp Gly Asp Val Val Gln Val Asp Leu
210                 215                 220
Met Glu Ser Arg Tyr Ser Thr Gly Gly Val Asp Gly Thr Pro Thr Gly
225                 230                 235                 240
Val Trp Thr Pro Met Arg Glu Ser Trp Gly Ser Ile Trp Arg Leu Asp
                245                 250                 255
Thr Asn His Pro Leu Gln Gly Pro Phe Ser Leu Arg Ile Thr Asn Glu
            260                 265                 270
Ser Gly Lys Thr Leu Ile Ala Asp Gln Val Ile Pro Ala Asp Trp Gln
        275                 280                 285
Pro Asn Thr Val Tyr Ser Ser Ile Val Gln Phe
    290                 295
```

EXPANSIN POLYNUCLEOTIDES, RELATED POLYPEPTIDES AND METHODS OF USE

This application claims benefit of provisional application 60/285,050 filed Apr. 19, 2001.

This research was sponsored by the US Department of Energy grant DE-FG02-84ER13179 and the US Department of Agriculture grant PENR-9601307. The United States Government has certain rights in this invention.

FIELD OF THE INVENTION

The present invention relates to novel expansin proteins, compositions comprising such proteins, isolated polynucleotides encoding these novel expansins, methods for using the polynucleotides and proteins of the invention and methods for identifying, isolating and purifying expansins.

BACKGROUND OF THE INVENTION

Cell wall proteins play important roles in regulating cell wall extensibility which in turn controls cell enlargement. Among cell wall proteins studied to date, expansins are unique in their ability to induce immediate cell wall extension in vitro and cell expansion in vivo. Expansins are extracellular proteins that promote plant cell wall enlargement, evidently by disrupting noncovalent bonding between cellulose microfibrils and matrix polymers (McQueen-Mason, S., et al., (1994) *Proc. Natl. Acad. Sci USA* 91:6574–6578; McQueen-Mason, S., et al., (1992) *Plant Cell* 4:1425–1433).

Since their first isolation from cucumber hypocotyls, expansin proteins have been identified in many plant species and organs on the basis of activity assays and immunoblotting. Examples include tomato leaves, oat coleoptiles, maize roots, rice internodes, tobacco cell cultures, and various fruits. The original sequencing of cucumber expansin cDNAs has impacted our understanding of expansins in several respects. First, expansin genes have now been identified in many other plant species, and they appear to be restricted largely to the plant kingdom. Second, expansins comprise a large multigene family in the plant species. For example, in *Arabidopsis*, 31 expansin genes have been identified. Third, studies of expression and localization of expansin mRNA are providing new insights and hypothesis concerning the developmental roles of specific expansin genes. And fourth, sequence comparisons have led to the discovery that another group of proteins known previously as group-1 grass pollen allergens, have expansin activity. These pollen-specific proteins are closely related to a group of sequences known primarily from expressed sequence tag (EST) databases. These EST sequences, together with the group-1 pollen allergens, have now been classified as beta-expansins, whereas the original group of expansins are now classified as alpha-expansins. The alpha-expansins are described in U.S. Pat. Nos. 5,959,082 and 5,990,283 to Cosgrove et al., which are herein incorporated by reference. Beta-expansins, in general, are the subject of a previously filed U.S. patent application Ser. No. 09/071,252 filed May 1, 1998. Although these two expansin families have only about 20% amino acid identity, they are similar in size, they share a number of conserved motifs, and they have similar wall-loosening activities.

To date, most studies have focused on alpha-expansins, and limited work has been done on beta-expansins. A soybean cytokinin-induced gene known as CIM1 is now classified as a beta-expansin, but the biological function of the CIM1 protein is uncertain. The maize group-1 pollen allergen, Zea m1, has wall-loosening activity with high specificity for grass cell walls. This beta-expansin is hypothesized to aid fertilization by loosening the cell walls of the stigma and style, thereby facilitating penetration of the pollen tube. Many other beta-expansin sequences are found in the rice EST databases, and most of these sequences come from cDNA libraries made from young seedlings and other plant materials that do not contain pollen. Thus, their biological functions clearly differ from those of the group-1 pollen allergens. These so-called vegetative beta-expansins are hypothesized to function in cell enlargement and other processes where wall loosening is required. It is notable that the rice EST collection contains at least 75 entries representing at least 10 distinct beta-expansin genes. In contrast, only a single *Arabidopsis* EST is classified as a beta-expansin (although a total of five beta-expansin genes are found in the *Arabidopsis* genome). The disparity in the number of beta-expansin entries in the rice and *Arabidopsis* EST collection, together with the specificity of Zea m1 activity for grass walls, leads to the proposal that beta-expansins have evolved specialized function in conjunction with the evolution of the grass cell wall, which has a distinctive set of matrix polysaccharide and structural proteins compared with other land plants. If this is true, one would expect to find an abundance of beta-expansin homology in other grasses, with expression in many tissues beside pollen. In this application, we describe expansins from maize.

SUMMARY OF THE INVENTION

The present invention relates to novel beta expansins, compositions thereof and isolated polynucleotides encoding the same, as well as conservatively modified variants thereof.

In one aspect, the invention relates to a polypeptide belonging to a class of expansins. Sequences of the novel polypeptides of the invention are disclosed in SEQ ID NO: 2 or 4. The invention also comprises conservatively modified variants of these sequences, an amino acid sequence comprising at least 20 contiguous bases from these sequences, a polypeptide sequence comprising at least 55% sequence identity from these sequences, a polypeptide encoded by the nucleotide sequences of the invention, and all conservatively modified variants of these sequences.

In another aspect, the invention relates to a polynucleotide encoding any of the polypeptides of the invention, including but not limited to SEQ ID NO:1 or 3 as well as a polynucleotide comprising at least 20 contiguous bases from the polynucleotides of the invention, a polynucleotide comprising at least 55% sequence identity to the polynucleotides of the invention, a polynucleotide comprising at least 20 contiguous nucleotides of the polynucleotides of the invention and which hybridize under conditions of high stringency to these sequences, all of which encode a protein which has expansin activity as demonstrated by the assays disclosed herein as well as their complements. The polynucleotide may be DNA, RNA, or a combination of the two.

The invention also relates to an expression construct, (comprising the polynucleotide of the invention operably linked to regulatory elements capable of regulating expression in a plant cell) a vector, a host cell and/or a transgenic plant comprising the polynucleotides of the invention.

In yet another aspect, the invention relates to a method of altering physical properties of the plant cell wall or any cell wall products derived from plant material, for example paper or textile using the polynucleotides of the invention to create plants with these properties or using compositions comprising the polypeptides of the invention.

In a further aspect, the invention relates to a method of identifying, isolating and purifying an expansin protein or a polynucleotide encoding such protein from other plant species, or types by using the polynucleotides or polypeptides of the invention.

DESCRIPTION OF THE DRAWINGS

FIG. 2 depicts the polynucleotide sequence of ExpB2 corresponding to SEQ. ID NO:1.

FIG. 3 depicts the amino acid sequence of ExpB2 corresponding to SEQ ID NO:2.

FIG. 4 depicts the polynucleotide sequence of ExpB4 corresponding to SEQ ID NO:3.

FIG. 5 depicts the amino acid sequence of ExpB4 corresponding to SEQ ID NO:4.

DETAILED DESCRIPTION OF THE INVENTION

Figure 1:
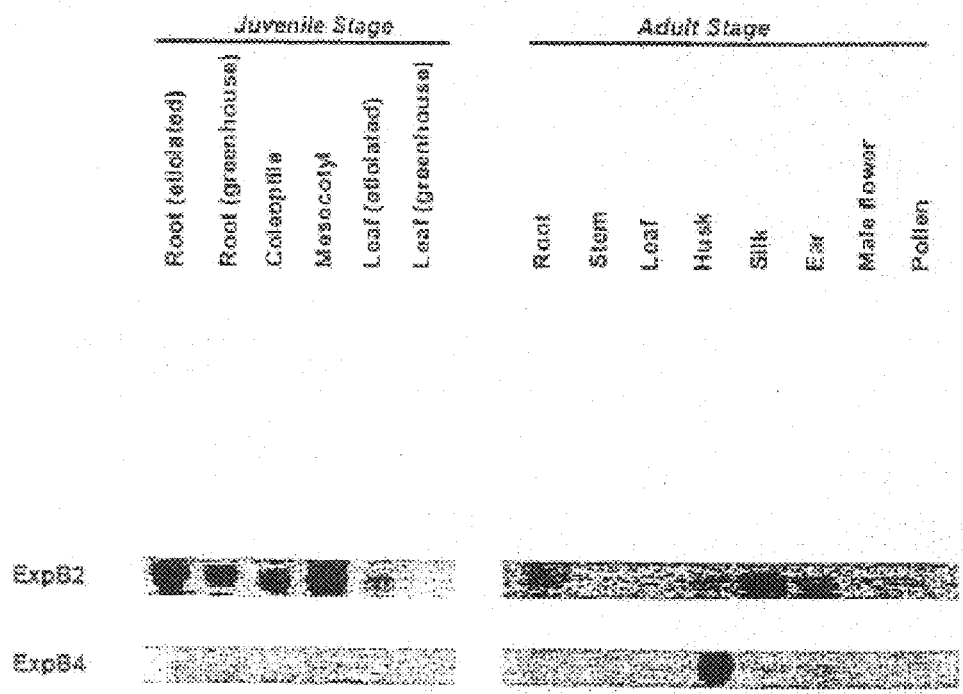
FIG. 1 shows Northern-blot analysis for expansins discussed in the present application. Expansins according to the present invention are indicated by ExpB2 and ExpB4.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, *Botany: Plant Biology and Its Relation to Human Affairs* (1982) John Wiley; *Cell Culture and Somatic Cell Genetics of Plants*, Vol. 1 (I. K. Vasil, ed. 1984); R. V. Stanier, J. L. Ingraham, M. L. Wheelis, and P. R. Painter, *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); and the series *Methods in Enzymology* (S. Colowick and N. Kaplan, eds., Academic Press, Inc.).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology*: Principles and applications, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine, one exception is *Micrococcus rubens*, for which GTG is the methionine codon (Ishizuka, et al., *J. Gen'l Microbiol,* 139:425–432 (1993)) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90%, preferably 60–90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1× SSC and 0.1% sodium dodecyl sulfate at 65° C.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray et al. *Nucl. Acids Res.* 17: 477–498 (1989) and herein incorporated by reference). Thus, the maize preferred codon for a particular amino acid might be derived from known gene sequences from maize. Maize codon usage for 28 genes from maize plants is listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" or "recombinantly engineered cell" is meant a cell, which contains a vector and supports the replication and/or expression of the expression vector. Host cells may be prokaryotic cells such as *E. coli*, or eukaryotic cells such as yeast, *Pichia*, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "expansin nucleic acid" means a nucleic acid comprising a polynucleotide ("expansin polynucleotide") encoding an expansin polypeptide. The term exapnsin, B2 expansin, or B4 expanisn, unless otherwise stated can encompass both expansin B2 and/or B4 and any functional, truncated versions of these sequences as well as conservatively modified variants and antisense polynucleotides designed to inhibit the same.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual,* 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis,*

*Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium,* and *Triticum.* A particularly preferred plant is *Zea mays.*

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium.* Examples are promoters that preferentially initiate transcription in certain tissues, such as leaves, roots, seeds, fibres, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "B2, B4, ExpB2 and/or ExpB4 expansin peptide or polypeptide" refers to one or more amino acid sequences of the novel beta expansins disclosed herein. The term is also inclusive of fragments, variants, homologs, alleles or precursors (e.g., preproproteins or proproteins) thereof.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60–90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m$=81.5° C.+16.6 (log M)+0.41 (% GC)–0.61 (% form) –500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). Unless otherwise stated, in the present application high stringency is defined as hybridization in 4× SSC, 5× Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1× SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (Best Fit) of Smith and Waterman, Adv. Appl. Math may conduct optimal alignment of sequences for comparison 2: 482 (1981); by the homology alignment algorithm (GAP) of Needleman and Wunsch, *J. Mol. Biol.* 48: 443 (1970); by the search for similarity method (Tfasta and Fasta) of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The preferred program to use for optimal global alignment of multiple sequences is PileUp (Feng and Doolittle, *Journal of Molecular Evolution*, 25:351–360 (1987) which is similar to the method described by Higgins and Sharp, *CABIOS*, 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci USA* 89:10915).

Unless otherwise stated, sequence identity/similarity values provided herein refer to the value obtained using the BLAST 2.0 suite of programs using default parameters. Altschul et al., *Nucleic Acids Res.* 25:3389–3402 (1997).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Clayerie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has between 50–100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 40–100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terms "substantial identity" in the context of a peptide indicates that a peptide comprises a sequence with between 55–100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The present invention relates to novel proteins belonging to a class of proteins designated beta-expansins, a composition comprising such proteins, polynucleotides encoding the beta-expansins of the invention (and vectors, host cells and plants containing such polypeptides), a method for using the polynucleotides and proteins of the invention to alter plant cell wall characteristics, and a method for identifying, isolating and purifying other novel expansins. Beta-expansins of the invention, and polynucleotides encoding beta-expansins, may be of natural origin, isolated and purified or recombinantly produced.

Beta-expansins have the property of altering physical properties of a plant cell wall. For purposes of the present disclosure, "altering physical characteristics of a plant cell wall" includes loosening or expanding cell walls, altering cell wall mechanical strength, altering the bonding relationship between the components of the cell wall and/or altering the growth of the plant cell wall. This property of beta-expansins may be determined by using assays well known in the art, such as cell-wall extension and stress relaxation assays. Induction of cell wall extension (creep) and an increase in the stress relaxation spectrum of the wall are diagnostic for expansins. Expansins show an effect in these assays at, for example, a dosage of 1 part (and above) protein to 1,000 to 10,000 parts cell wall (on a dry weight basis). Beta-expansins of the invention are similar to alpha-expansins described in U.S. Pat. Nos: 5,959,08, and 5,990,283 entitled "PROTEIN CATALYZING THE EXTENSION OF PLANT CELL WALLS", U.S. Pat. No. 6,326,470, ENHANCEMENT OF ACCESSIBILITY OF CELLULOSE BY EXPANSINS", and U.S. Pat. No. 6,255,466, PURIFIED EXPANSIN PROTEIN, the disclosures of which are incorporated herein by reference, in that they both have the property of inducing stress relaxation and extension of plant cell walls. However, beta-expansins have low amino acid sequence similarity with alpha-expansins, which is about 25% as determined by BLAST or FASTA algorithms. Furthermore, beta-expansins are more effective on grass cell walls than on dicotyledon plant cell walls. In contrast alpha-expansins are more effective on dicotyledon plant cells walls than on grass cell walls. Since it is known that monocot and dicot cell walls differ in their chemical composition, it is likely that beta and alpha expansins act on different components of the plant cell wall.

The present invention also relates to a composition containing a beta-expansin polypeptide fo the inveniton. The composition has the property of altering the physical characteristics of a plant cell wall or of any material containing such cell walls (e.g. paper, textile). Preferably, the composition contains an acid medium. Preferably, the pH of the acid medium is in the range of 3.0–5.5 and additionally may comprise a sulfhydryl reducing agent. The pH range is more preferably about 3.5–5 and most preferably is about 4.0. Suitable acid buffers include acetate citrate and other orizanic acids.

Buffer concentrations in the composition of the invention are preferably from about 20 to about 100 MM. In other embodiments of the invention at least 1 mM or at most 500 mM is used. Urea, for example at about 1–2 M, may act synergistically with expansins. Calcium chelators such as EGTA, EDTA, CDTA, at for example about 1–50 mM can aid expansin action. Thiol reductants such as dithiothreitol or bisulfite, for example at about 1–10 mM may also be used. However, the only essential ingredient is the expansin protein (for example at a concentration of about 1–10 micrograms per mL). In one embodiment, at least 0.1 micrograms per mL may be used (higher than 10 micrograms per mL is very effective, but may be wasteful of the protein).

The present invention also relates to polynucleotides encoding the polypeptides of the invention. A "polynucleotide" is intended to include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids as well as "protein nucleic acids" (PNA) formed by conjugating bases to an amino acid backbone. This also includes nucleic acids containing modified bases, for example thio-uracil, thio-guanine and fluoro-uracil.

Polynucleotides encoding beta-expansins of the invention may be isolated from both monocotyledon and dicotyledon plants. Other plant sources, such as gynnosperms, ferns and 5 mosses, are also within the scope of the present invention. However, beta-expansin-encoding polynucleotides produced by using recombinant DNA technology are also within the scope of the present invention. In one embodiment, a polynucleotide encodes a beta-expansin of a monocotyledon origin, i.e., it has a nucleotide sequence identical to the one originally found in a monocotyledon plant (maize).

Conservatively modified variants are of polynucleotides encoding the beta-expansins of the invention are also within the scope of the present invention.

The polynucleotides of the invention may be isolated directly from cells using appropriate labeled probes containing, for example, regions of high conservation among expansins.

Alternatively PCR can be used to produce the polynucleotides of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

Given its properties to affect the plant cell wall, beta-expansins of the invention find use in a number of industries. For example, beta-expansins can be used in the paper industry for paper recycling.

The advantages of using expansins for paper recycling include the following: the protein is nontoxic and environmentally innocuous; it could substitute for current harsh chemical treatments which are environmentally noxious. The protein is effective on paper products which are now recalcitrant to current recycling processes. Its use could expand the range of recyclable papers. Because the protein acts at moderate temperature and in mild chemical environments, degradation of paper fibers during recycling should be reduced. This should allow for recycled paper fibers with stronger mechanical properties and with the ability to be recycled more often than is currently practical. Moreover, savings in energy costs associated with heating and beating the paper may be realized.

Other modes of application of R-expansins include production of virgin paper. Pulp for virgin paper is made by disrupting the bonding between plant fibers. Beta-expansins may be useful in the production of paper pulp from plant tissues.

Use of expansins could substitute for harsher chemicals now in use and thereby reduce the financial and environmental costs associated with disposing of these harsh chemicals. The use of expansins could also result in higher quality plant fibers because they would be less degraded than fibers currently obtained by harsher treatments.

Beta-expansins may be also used to make harsh plant fibers, such as wood fibers accessible as a biomass source for alcohol production.

To achieve this result, beta-expansins may be added alone, or in combination with alpha-expansins, to an alcohol manufacturing process. Alternatively, a plant intended as a source for making alcohol may be transformed with the polynucleotides of the invention hence making a plant having softer fibers that are easier to process. Methods for introducing polynucleotides of the invention into plant cell, and regenerating plants therefrom are well known in the art and are described, for example, in: Plant Molecular Biology, Ed. R. R. D. Croy, Bios Scientific Publishers, Academic Press, 1993.

Beta-expansins of the invention may also be used to alter the growth behavior of plants transformed with a beta-expansin encoding polynucleotide.

In another embodiment, the invention relates to a method for identifying, isolating and purifying the beta expansins of the invention. New expansins may be identified by assaying crude extracts of plant, fungal, or other origin for their ability to induce extension (creep) of cell walls from plants. Suitable plant walls materials include, but are not limited to, frozen/thawed/heat-inactivated specimens from cucumber hypocotyls or grass coleoptiles clamped under tension in an extensometer and incubated in an acidic buffer, such as 50 mM sodium acetate, pH 4.5. Active extracts may be further purified by combining extensometer assays with protein fractionation techniques such as HPLC, electrophoresis, and selective precipitation with ammonium sulfate, polyethylene glycol, antibodies, and other affinity matrices. In this way, new proteins with expansin activity may be identified and purified. New expansin genes may be cloned in many standard ways, such as the use of polymerase chain reaction (PCR) to amplify gene fragments or cDNA fragments, using primers based on the sequences disclosed herein. Alternatively, cDNA and genomic libraries made from plants, fungi or other biological materials may be synthesized and screened at low stringency (e.g. hybridization and washing in 3× SSC at 50-C using a nucleotide sequence encoding the conserved parts of the expansin protein).

The invention herein in its broadest sense contemplates the discovery of the existence of a beta expansin gene in plants that is associated among other things cell wall characteristics. The discovery of the existence of this type of gene creates numerous opportunities for manipulation of plant physical and chemical characteristics. Homologous proteins or mutants as described herein and as isolated form other plants are also intended to be within the scope of the invention.

In yet another embodiment the invention comprises regulatory sequences associated with the novel beta expansin polynucleotides of the invention. This regulatory region may be used to achieve expression of heterologous expasin encoding polynucleotides in plants.

The invention in one aspect comprises expression constructs comprising a DNA sequence which encodes upon expression a beta expansin gene product operably linked to a regulatory sequences such as a promoter to direct expression of the protein. These constructs are then introduced into plant cells using standard molecular biology techniques. The invention can be also be used for hybrid plant or seed production, once transgenic inbred parental lines have been established.

In another aspect the invention involves the inhibition of a beta expansin gene product in plants through introduction of a construct designed to inhibit the same gene product. The design and introduction of such constructs based upon known DNA sequences is known in the art and includes such technologies as antisense RNA or DNA, co-suppression or any other such mechanism. Several of these mechanisms are described and disclosed in U.S. Pat. No. 5,686,649 to Chua et. al, which is hereby expressly incorporated herein by reference. For example one may seek to improve stalk strength by inhibiting the expansin activity of a particular plant.

The methods of the invention described herein may be applicable to any species of plant.

The polynucleotides useful in the invention can be formed from a variety of different polynucleotides (e.g., genomic or cDNA, RNA, synthetic oligonucleotides, and polynucleotides), as well as by a variety of different techniques.

The present invention provides, inter alia, isolated nucleic acids of RNA, DNA, and analogs and/or chimeras thereof, comprising an B2 or B4 beta expansin polynucleotide.

The present invention also includes polynucleotides optimized for expression in different organisms. For example, for expression of the polynucleotide in a maize plant, the sequence can be altered to account for specific codon preferences and to alter GC content as according to Murray et al, supra. Maize codon usage for 28 genes from maize plants is listed in Table 4 of Murray, et al., supra.

The B2 or B4 beta expansin nucleic acids of the present invention comprise isolated B2 or B4 beta expansin polynucleotides which, are inclusive of:

(a) a polynucleotide encoding a B2 or B4 beta expansin polypeptide of the sequences shown in SEQ ID NOS: 1and 3, and conservatively modified and polymorphic variants thereof;

(b) a polynucleotide which encodes the polypeptide sequence shown in SEQ ID NOS 2 and 4, (c) a polynucleotide which selectively hybridizes to a polynucleotide of (a) or (b);

(d) a polynucleotide having at least 50%, 60% 70% 80% of 80% sequence identity with polynucleotides of (a) or (b);

(e) complementary sequences of polynucleotides of (a), (b), or (c); and (f) a polynucleotide comprising at least 25 contiguous nucleotides from a polynucleotide of (a), (b), (c), or (d).

It is recognized that the sequences of the invention can be used to isolate corresponding sequences in other organisms.

Methods such as PCR, hybridization, and the like can be used to identify sequences having substantial sequence similarity to the sequences of the invention. See, for example, Sambrook, et al., (1989) *Molecular Cloning: A Laboratory Manual* (2d ed., Cold Spring Harbor Laboratory Press, Planview, N.Y.) and Innis et al., (1990) *PCR Protocols: Guide to Methods and Applications* (Academic Press, New York). Coding sequences isolated based on their sequence identity to the entire fumonisin degrading coding sequences set forth herein or to fragments thereof are encompassed by the present invention.

The nucleotide constructs of the present invention will share similar elements, which are well known in the art of plant molecular biology. For example, in each construct the DNA sequences of interest will preferably be operably linked (i.e., positioned to ensure the functioning of) to a promoter which allows the DNA to be transcribed (into an RNA transcript) and will comprise a vector which includes a replication system. In preferred embodiments, the DNA sequence of interest will be of exogenous origin in an effort to prevent co-suppression of the endogenous genes.

Promoters (and other regulatory elements) may be heterologous (i.e., not naturally operably linked to a DNA sequence from the same organism). Promoters useful for expression in plants are known in the art and can be inducible, constitutive, tissue-specific, derived from eukaryotes, prokaryotes or viruses, or have various combinations of these characteristics.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in the cells/tissues of a plant critical to seed set and/or function and/or limits the expression of such a DNA sequence to the period of seed maturation in the plant. Any identifiable promoter may be used in the methods of the present invention which causes the desired temporal and spatial expression.

Any inducible promoter can be used in the instant invention. See Ward et al. *Plant Mol. Biol.*22: 361–366 (1993). Exemplary inducible promoters include, but are not limited to, that from the ACE1 system which responds to copper (Mett et al. *PNAS* 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et al., *Mol. Gen. Genet.* 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci U.S.A.* 88: 0421 (1991).

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., Plant Cell 2: 163–171 (1990)); ubiquitin (Christensen et al., Plant Mol. Biol 12: 619–632 (1989) and Christensen et al., Plant Mol. Biol. 18: 675–689 (1992)): pEMU (Last et al., Theor. Appl. Genet. 81: 581–588 (1991)); MAS (Velten et al., EMBO J. 3: 2723–2730 (1984)) and maize H3 histone (Lepetit et al., Mol. Gen. Genet. 231: 276–285 (1992) and Atanassova et al., Plant Journal 2 (3): 291–300 (1992)).

The ALS promoter, a Xbal/Ncol fragment 51 to the *Brassica napus* ALS3 structural gene (or a nucleotide sequence that has substantial sequence similarity to said Xbal/Ncol fragment), represents a particularly useful constitutive promoter. See PCT application WO96/30530.

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Sullivan, T., "Analysis of Maize Brittle-1 Alleles and a Defective Suppressor-Mutator-Induced Mutable Allele", *The Plant Cell*, 3:1337–1348 (1991), Becker et al., *Plant Mol. Biol.*20: 49 (1992), Close, P. S., Master's Thesis, Iowa State University (1993), Knox, C., et al., "Structure and Organization of Two Divergent Alpha-Amylase Genes From Barley", *Plant Mol. Biol.* 9: 3–17 (1987), Lerner et al., *Plant Physiol.*91: 124–129 (1989), Fontes et al., *Plant Cell* 3: 483–496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Selection of an appropriate vector is relatively simple, as the constraints are minimal. The minimal traits of the vector are that the desired nucleic acid sequence be introduced in a relatively intact state. Thus, any vector which will produce a plant carrying the introduced DNA sequence should be sufficient. Typically, an expression vector contains (1) prokaryotic DNA elements encoding for a bacterial replication origin and an antibiotic resistance marker to provide for the growth and selection of the expression vector in a bacterial host; (2) DNA elements that control initiation of transcription, such as a promoter; (3) DNA elements that control the processing of transcripts such as transcription termination/polyadenylation sequences; and (4) a reporter gene. Useful reporter genes include β-glucuronidase, β-galactosidase, chloramphynical acetyltransferase, luciferase, kanamycin or the herbicide resistance genes PAT and BAR. Preferably, the reporter gene is kanamyacin or the herbicide resistance genes PAT and BAR. The BAR or PAT gene is used with the selecting agent Bialaphos, and is used as a preferred selection marker gene for plant transformation (Spencer, et al. (1990) *J. Thero. Appl'd Genetics* 79:625–631).

One commonly used selectable marker gene for plant transformation is the neomycin phosphotransferase II (nptll) gene, isolated from transposon Tn5, which when placed under the control of plant regulatory signals confers resistance to kanamycin. Fraley et al., *Proc. Natl. Acad Sci. USA.,* 80: 4803 (1983). Another commonly used selectable marker gene is the hygromycin phosphotransferase gene which confers resistance to the antibiotic hygromycin. Vanden Elzen et al., *Plant Mol. Biol.,* 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.,* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green, p. 1–4 (1993) and Naleway et al., *J. Cell Biol.* 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

A general description of plant expression vectors and reporter genes can be found in Gruber, et al. (Gruber et al. (1993) Vectors for Plant Transformation. In: *Methods in Plant Molecular Biology and Biotechnology.* Glich et al., eds. (CRC Press), pp. 89–119.

Expression vectors containing genomic or synthetic fragments can be introduced into protoplast or into intact tissues or isolated cells. Preferably, expression vectors are introduced into intact tissue. General methods of culturing plant tissues are provided for example by Maki, et al. (Maki, et al. (1993) Procedures for Introducing Foreign DNA into Plants: In: *Methods in Plant Molecular Biology & Biotechnology*; Glich et al. eds. (CRC Press), pp. 67–88; Philips, et al. (1988) Cell-Tissue Culture and In Vitro Manipulation. In *Corn & Corn Improvement,* 3rd ed. Sprague, et al. eds. (American Society of Agronomy Inc.), pp. 345–387).

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology,* Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick, B. R. and Thompson, J. E. Eds. (CRC Press, Inc., Boca Raton, 1993) pages 89–119.

*Agrobacterium*-mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant.* Sci.10: 1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,591,616, issued Jan. 7, 1997.

Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and maize. Hiei et al., The Plant Journal 6: 271–282 (1994); U.S. Pat. No. 5,591,616, issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 mm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559–563 (1988), Sanford, J. C., *Physiol Plant* 79: 206 (1990), Klein et al., *Biotechnology* 10: 268 (1992). In maize, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.,* 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.*199: 161 (1985) and Draper et al., *Plant Cell Physiol.*23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495–1505 (1992) and Spencer et al., *Plant Mol. Biol.* 24: 51–61 (1994).

Following transformation of target tissues, expression of the above-described selectable marker genes allows for preferential selection of transformed cells, tissues and/or plants, using regeneration and selection methods now well known in the art.

After transformation of a plant cell or plant, plant cells or plants transformed with the desired DNA sequences integrated into the genome can be selected by appropriate phenotypic markers. Phenotypic markers are known in the art and may be used in this invention.

Confirmation of transgenic plants will typically be based on an assay or assays or by simply measuring stress response. Transformed plants can be screened by biochemical, molecular biological, and other assays. Various assays may be used to determine whether a particular plant, plant part, or a transformed cell shows an increase in enzyme activity or carbohydrate content. Typically, the change in expression or activity of a transformed plant will be compared to levels found in wild type (e.g., untransformed) plants of the same type. Preferably, the effect of the introduced construct on the level of expression or activity of the endogenous gene will be established from a comparison of sibling plants with and without the construct. Protein levels can be measured, for example, by Northern blotting, primer extension, quantitative or semi-quantitative PCR (polymerase chain reaction), and other methods well known in the art (See, e.g., Sambrook, et al. (1989). *Molecular Cloning, A Laboratory Manual*, second edition (Cold Spring Harbor Laboratory Press), Vols. 1–3). Protein can be measured in a number of ways including immunological methods (e.g., by Elisa or Western blotting). Protein activity can be measured in various assays as described in Smith (Smith, A. M. (1990). In: *Methods in Plant Biochemistry*, Vol. 3, (Academic Press, New York), pp. 93–102).

Normally, regeneration will be involved in obtaining a whole plant from a transformation process. The term "regeneration" as used herein, means growing a whole plant from a plant cell, a group of plant cells, a plant part, or a plant piece (e.g., from a protoplast, calys, or a tissue part).

The foregoing methods for transformation would typically be used for producing transgenic inbred lines. Transgenic inbred lines could then be crossed, with another (non-transformed or transformed) inbred line, in order to produce a transgenic hybrid plant. Alternatively, a genetic trait which has been engineered into a particular line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid plant containing a foreign gene in its genome into a line or lines which do not contain that gene. As used herein, "crossing" can refer to a simple X by Y cross, or the process of backcrossing, depending on the context.

Parts obtained from the regenerated plant, such as flowers, pods, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences.

Once a transgenic plant is produced having a desired characteristic, it will be useful to propagate the plant and, in some cases, to cross to inbred lines to produce useful hybrids.

In seed propagated crops, mature transgenic plants may be self crossed to produce a homozygous inbred plant. The inbred plant produces seed containing the genes for the newly introduce trait. These seeds can be grown to produce plants that will produce the selected phenotype.

This invention further contemplates the identification of other polynucleotides encoding B2 or B4 beta expansin type proteins. Methods for identifying these other polynucleotides are known to those of skill in the art and will typically be based on screening for other cells which express the same. Nucleotide sequences encoding this protein are easily ascertainable to those of skill in the art through Genbank or the use of plant protein codon optimization techniques known to those of skill in the art and disclosed in the references cited herein (for example see EPO publication number 0682115A1 and Murray et al., 1989, *Nuc Acid Res.*, Vol. 17 No. 2, pp 447–498, "Codon Usage in Plant Genes". It is preferred to use the optimized coding sequences, for the plant recipient species. These sequences can be used not only in transgenic protocols but as tags for marker-assisted selection in plant breeding programs.

The present invention also provides antibodies capable of binding to B2 or B4 beta expansin from one or more selected species. Polyclonal or monoclonal antibodies directed toward part or all of a selected B2 or B4 beta expansin gene product may be prepared according to standard methods. Monoclonal antibodies may be prepared according to general methods of Köhler and Milstein, following standard protocols.

Purified B2 or B4 beta expansin or fragments thereof, may be used to produce polyclonal or monoclonal antibodies which may serve as sensitive detection reagents for the presence and accumulation of the proteins in cultured cells or tissues and in intact organisms. Recombinant techniques enable expression of fusion proteins containing part or all of a selected B2 or B4 beta expansin. The full length protein or fragments of the protein may be used to advantage to generate an array of monoclonal or polyclonal antibodies specific for various epitopes of the protein, thereby providing even greater sensitivity for detection of the protein.

Polyclonal or monoclonal antibodies immunologically specific for B2 or B4 beta expansin may be used in a variety of assays designed to detect and quantitate the proteins. Such assays include, but are not limited to, (1) immunoprecipitation followed by protein quantification; (2) immunoblot analysis (e.g., dot blot, Western blot) (3) radioimmune assays, (4) nephelometry, turbidometric or immunochromatographic (lateral flow) assays, and (5) enzyme-coupled assays, including ELISA and a variety of qualitative rapid tests (e.g., dip-stick and similar tests).

Appropriate host cells include bacteria, archaebacteria, fungi, especially yeast, and plant and animal cells. Of particular interest are *E. coli, B. subtilis, Saccharomyces cerevisiae, Saccharomyces carlsbergensis, Schizosaccharomyces pombi*, SF9 cells, C129 cells, 293 cells, *Drosophila* cell lines, *Neurospora, Pichia*, and CHO cells, COS cells, HeLa cells, and immortalized mammalian myeloid and lymphoid cell lines. Preferred replication systems include M13, ColEl, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced β-expansins or derived peptides and polypeptides. For plant transformation, DNA may be cloned into cassettes based on T-DNA plasmids, propagated in *E. coli* or *Agrobacterium*, and used to stably transform plants by the *Agrobacterium* method. Alternatively, DNA may be inserted into suitably modified plant viruses, such as tobacco mosaic virus. and used to produce recombinant protein by infection of tobacco plants or other sensitive plant species.

Vectors may also include a transcription regulatory element (a promoter) operably linked to the β-expansin sequence. The promoter may optionally contain operator portions and/or ribosome binding sites. Non-limiting examples of bacterial promoters compatible with *E. coli* include: trc promoter, alpha-lactamase (penicillinase) promoter; lactose promoter; tryptophan (trp) promoter; arabinose BAD operon promoter; lambda-derived PI promoter and N gene ribosome binding site; and the hybrid tac promoter derived from sequences of the trp and lac UV5 promoters. Non-limiting examples of plant promoters include: CaMV 35S, PR1, PR, auxin-inducible promoter, ethylene-inducible promoter, heat-shock promoter, seed storage protein promoter.

Non-limiting examples of yeast promoters include 3-phosphoglycerate kinase promoter, glyceraldehyde-3-phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included.

Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

Polyclonal or monoclonal antibodies that immunospecifically interact with Ra1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

The following examples and intended to further illustrate the invention and are not intended to limit the invention in any way. The examples and discussion herein may specifically reference maize, however the teachings herein are equally applicable to any other plant. The invention is further described in the following non-limiting examples. All patents, patent applications and publications cited herein are hereby incorporated by reference. In case of inconsistencies the present disclosure governs.

EXAMPLES

Example 1

Plant Materials

Inbred maize plants were used in this study. For analysis of gene expression, we harvested tissues from maize plants at different growth stages. For etiolated plant materials, a row of seeds was arranged on germination paper (Anchor Paper, MN). The paper was rolled to form a tube and placed vertically in a 2-liter beaker containing 200 mL distilled water. The beaker was loosely covered with another container to reduce water loss. After 96 h at 29° C. in the dark, roots (apical 20 mm), coleoptiles, mesocotyls, young leaves of maize seedlings were harvested under dim green light. For the greenhouse-grown plants, seeds were germinated in the greenhouse in soil (Pro-Mix, Geiger, PA). Young leaves and the whole primary roots of one-week-old seedlings were collected. Several seedlings were transplanted into 6-liter pots for further cultivation. Four days after silks appeared, the youngest leaf near the tassel, the stem (the internode below the tassel), several young adventitious roots (whole), male flowers, pollen, silk, husk (inner layers) and the whole unpollinated ear were harvested. Harvested tissues were immediately frozen in liquid nitrogen after collection and stored at 80° C. before removal for RNA or genomic DNA extraction.

Library Screening and Sequencing

A maize root cDNA library (Oklahoma City University) was first screened by plaque hybridization using a radiolabeled probe (a mixture of nine rice expansin cDNAs). Nylon membranes with lifted plaques were pre-hybridized in hybridization buffer (Amersham) at 60° C. overnight, then hybridized with the radioactive probe in the same buffer at 60° C. for 20 hours. Membranes were washed for 45 min once in 3× SSC, 45 min once in 1× SSC and 45 min twice in 0.1× SSC at 60°, then exposed to X-ray film (Fuji film, Japan) for 24 hour at room temperature. From about $1.5 \times 10^6$ plaques screened a total of 255 positive plaques were picked for further screening. After the secondary and tertiary screening, 64 positive plaques were chosen for DNA isolation. Based on the restriction digestion pattern, 16 different inserts were subcloned into the pUC18 plasmid for subsequent sequencing. Five inserts turned out to be unique maize expansin cDNAs. Further sequencing work with positive clones from a maize cDNA collection revealed another 7 unique expansin cDNAs. Sequences have been deposited in GenBank under the following accession numbers: AF332169-AF332181.

Sequence Analysis

DNA sequences were analyzed with DNAstar software (DNASTAR, Inc, WI). Predicted amino acid sequences were aligned by MEGALIGN (DNAstar) using the Clustal method with the PAM250 residue weight table and default parameters. The phylogenetic tree was based on this alignment, using the neighbor joining method with Poisson-corrected distances (MEGA2 software). Signal peptides were predicted with the SignalP program (Henrik et al., 1997).

Hybridization Analysis

A PCR-amplified 3'-UTR region of each cDNA was used as a gene-specific probe (see below for Exp2 and Exp4) and $P^{32}$-labeled probes were prepared with a Rediprime kit (Amersham, IL). Plasmid DNA containing cDNA insert was dotted onto a nylon membrane to make an array of 1, 0.1, and 0.01 ng DNA for each expansin. The arrays were then hybridized to each gene-specific probe to test the specificity of the probe.

Primer sets for gene-specific probe synthesis.

```
ExpB2
5'AGCTAGCTGGTTTGCGCC3'      (SEQ ID NO:5) length-296 bp
5'AAGCAACAGTGGGCGGG3'       (SEQ ID NO:6)

ExpB4
5'CCTGAAAAGAGAAATACCG3'     (SEQ ID NO:7) length-213 bp
5'GTATCAAATTACCGGCATG3'     (SEQ ID NO:8)
```

For Southern blot analysis, genomic DNA was isolated from the shoots of etiolated maize seedlings with the CTAB method. Ten micrograms of DNA was digested with EcoRI, BamHI, or HindIII at 37° C. overnight, separated on a 0.8% agarose gel and vacuum-blotted to nylon membrane. For northern blot analysis, total RNA was extracted from plant tissues with TRIzol reagent (GibcoBRL, MD) using the manufacturer's instruction. Twenty micrograms of total RNA was separated on a 1% denatured agarose gel (6.5% formaldehyde, v/v) and vacuum-transferred to nylon membrane.

A set of blots consisting of one dot-blot, one Southern blot and two northern blots (one for young seedlings and one for adult stage), was processed together for hybridization to each of the 13 gene-specific probes. Blots were pre-hybridized in Ultrahyb solution (Ambion, TX) at 60° C. overnight and hybridized to the probe in the same solution at 60° C. for 20 h. The blots were washed at 65° C. for 20 min twice in 5% SEN (5% SDS, 1 mM EDTA, 40 mM $Na_2HPO_4$), and for 20 min once in 1% SEN (1% SDS, 1 mM EDTA, 40 mM $Na_2HPO_4$). Blots were exposed to phosphor screens (Molecular Dynamics) overnight at root temperature.

Sequence Analysis

We isolated and sequenced 13 distinct expansin cDNAs in this study. Ten of these maize cDNAs are predicted to encode the complete expansin protein and are probably full length or nearly full length cDNAs. Each of the 13 cDNAs has a unique 3'-UTR, so we conclude that they correspond to 13 distinct genes in the maize genome. This is also supported by Southern blot analysis, below. Each of the encoded proteins is predicted to have a signal peptide. The longest and the shortest signal peptides are 29 and 18 amino acid for Exp3 and Exp5, respectively; the average length is 24 amino acids. The predicted mature protein (after cleavage of the signal peptide) varies from 208 amino acids (Exp5) to 284 amino acid (ExpB4). This is a larger variation in expansin protein structure than seen heretofore in other plants.

Upon sequence analysis we have divided the 13 cDNAs into two groups, alpha expansins (5 cDNAs, named Exp1 to Exp5) and beta-expansins (8 cDNAs, named ExpB1 to ExpB8). Alignment of the predicted protein sequences shows that both groups of cDNAs contain the highly conserved regions that are diagnostic for expansins, including a series of conserved C (Cys) residues, an HFD (His-Phe-Asp) motif, and four W (Trp) residues near the carboxy-terminus. For the conserved Cys residues, eight were very well conserved in alpha-expansins, and 6 of the 8 Cys residues were conserved in the beta-expansin group. This difference in Cys residues between a- and b-expansins corresponds to the absence of approximately 14 amino acids in the b-expansin group and appears to be a consistent difference between the two groups of expansins. Other conserved differences between a- and b-expansins are highlighted in FIG. 1. Notably, the b-expansins have a predicted N-glycosylation site near the amino-terminus and in most, but not all, cases a second predicted glycosylation site near the carboxy terminus; in contrast, a-expansins lack glycosylation motifs.

The distinction between a- and b-expansin proteins is also readily apparent in the corresponding sequence-based phylogenetic tree, which shows the two families to be deeply divided from each other, with ~25% identity between the two families. In pair-wise comparisons within each family, high sequence similarity is typical of a-expansins (from 57–83% identity) while the b-expansins tend to be more divergent from each other (28–76% identity). The greater degree of sequence conservation in the a-expansin family can also be seen by inspection of the conserved residues.

Although most of the predicted proteins appeared to be rather typical for a- and b-expansins, some unusual features of ExpB4, Exp2, and Exp5 are worth noting. The predicted mature ExpB4 protein contains an unusual extension of ~53 amino acids at its amino terminus. This extension is highly basic (13 basic residues, no acidic residues; predicted pI of the extension is 11.6) and contains 13 Pro residues (25%). A BLAST search shows this short extension to be 40–50% identical with sequences from teosinte, rice, and maize encoding hydroxyproline-rich glycoproteins. These are structural proteins of the cell wall. The predicted mature form of Exp2 likewise has a short extension (25 amino acids) at its amino terminus, and this extension is rich in His, Gly, Pro and Arg residues. No significant sequence similarities were found in BLAST searches of GenBank when queried with this extension peptide. Exp5 is unusual in that a highly conserved motif (HATFYG or minor variations thereof) typically found at the amino-terminus of a-expansins is missing.

Southern Analysis

Since the 3'-UTR is the most divergent region of expansin cDNAs, we used them as gene-specific probes for Southern and northern blot analysis. A dot-blot analysis was first used to test the specificity of each probe. Except for probes from ExpB2 and ExpB8, all probes showed no cross-reaction with any other cDNA sequences at a level of 0.1 ng target DNA. Under the stringent conditions used, most probes could produce good signal even when the target DNA was only 0.01 ng. Probe for ExpB3 was an exception. It gave very week signal even when the target DNA was 0.1 ng. Probes from ExpB2 and ExpB8 showed cross-reaction with each other's cDNA at a level of 0.1 ng target DNA. These two cDNAs share very high sequence homology in their coding region, with 97.5% identity in nucleotide sequence. The encoded proteins differ from each other at only 3 amino acids in the sequences available (ExpB2 is a partial cDNA). Their 3'-UTRs are 74% identity over 127 bp, with a stretch of 65 bp having 96% identity. This degree of similarity for expansin cDNAs is unusual in our experience and we suspected they might be alleles for the same gene, but Southern analysis (below) indicates they are distinct genes.

The specificity of these probes was also demonstrated in Southern blots, which indicated that most, but not all, of these genes are present as single copy genes. For Exp1, Exp2, Exp3, Exp4, Exp5, ExpB3, ExpB6 and ExpB7, each probe detected a single band with different sizes in the three different enzyme digestions. The results indicate that each of these genes is probably present in the maize genome as a single copy.

The Southern blot also indicates that some of the probes hybridized with a second gene. There were double bands in the Southern blots for ExpB2 and ExpB8, which as described above are closely related in sequence. By comparing the two blots, it is apparent that the major band in each lane corresponded to the probed gene itself and the fainter band corresponded to the other cross-reacting gene. Judged from Southern blot results, the probe for ExpB8 is much more specific than the ExpB2 probe, since the second band is hardly visible on the Southern blot for ExpB8. A second faint band was visible on the Southern blots for ExpB1, indicating that the probe might be interacting with another gene. A recent blast search against the maize EST database identified two additional genes almost identical to ExpB1 in the coding region and with only a few nucleotide variations in the 3'-UTR. These two ESTs are listed as ExpB1b and ExpB1c in Table 3 while ExpB1 is listed as ExpB1a. The Southern blots for ExpB4 and ExpB5 indicate there might be a second closely related and linked gene in the maize genome for each of these b-expansins.

Expression Analysis

The expression patterns of these 13 expansin genes, studied by northern blotting with gene-specific probes, are complex (FIG. 1), with distinctive patterns for each gene. The strongest signals in the northern blots were found for Exp1, ExpB1, ExpB2 and ExpB8 (the Exp5 blot appears darker only because the phospor image sensitivity was raised to bring out the exposed bands).

The a-expansin Exp1 was detected in several organs from both juvenile and mature plants, whereas Exp5 was detected at low levels in juvenile roots and in the mesocotyl. The expression of the three other a-expansin genes (Exp2, Exp3, Exp4) was not detected in any tissue studied here. This negative result could mean that these genes are expressed at very low levels (as is typically the case in *Arabidopsis*; unpublished data), or that they require particular conditions to be expressed, or that they are expressed in organs or tissue types not sampled here. We assume they are indeed expressed genes because they were identified in cDNA libraries.

Six of the eight b-expansins were detected in northern blots. ExpB1 was detected with a very strong signal in pollen, as expected for the protein it encodes (*Zea* m1, a group-1 pollen allergen). The small signal seen in the male flower was probably due to the developing pollen in this organ. Another b-expansin which showed high specificity of expression is ExpB4, which gave a strong signal in young husks. In contrast to this high degree of specificity of expression, ExpB2 and ExpB8 were detected in many juvenile and mature organs. Because of high sequence similarity between these two genes, however, these northern blot results may be a composite of signals from both b-expansin mRNAs. The northern blot patterns are not identical for these two probes, however, so it is likely that these genes have distinct patterns of expression, but this point will need further work to resolve definitively. ExpB6 and ExpB7 were expressed in roots and mesocotyls. Additionally, ExpB7 was expressed at relatively high levels in the silk.

Some tissues are notable for high levels of expansin mRNA expression. These include roots and mesocotyls in juvenile plants and silks in adult plants. These organs were sampled at stages of rapid grow, which likely accounts for their high degree of expansin expression. Pollen gave the strongest signal of all, for ExpB1. Stem tissue is notable for its lack of detectable expansin gene expression; this is mostly likely due to sampling of the stem from a region lacking rapid growth.

We also analyzed the public maize EST databases for expansin gene expression and found an additional 17 sequence classes of expansins. One of the interesting observations from the table is that several ESTs with the highest frequency are from anther and pollen. This high frequency in pollen and anther libraries is consistent with the result of our northern blot analysis in FIG. 1, indicating that this gene is highly expressed in pollen.

Our results show that expansins in maize make up a diverse family of at least 30 genes (32 if we count ExpB1b-c separately). Among the 13 cDNAs studied, 8 encode b-expansin proteins and 5 encode a-expansin proteins. The b-expansin messages are expressed in a variety of organs, in some cases with high specificity, in other instances with wider expression. Analysis of the recently deposited maize ESTs confirms and extends this conclusion, bringing the total number of identified a-expansins in maize to 9 and the number of identified maize b-expansins to 18 (20 if we count ExpB1b-c separately). This is undoubtedly an incomplete inventory, as the Southern blots indicate there are additional expansin genes yet to be found in maize and many of the expansins are represented in the EST databases with low counts.

Our results indicate that b-expansins are more numerous and more abundantly expressed in maize than are a-expansins. Analysis of the rice EST database indicates that this situation is likely the case in rice too, and thus this may be a common characteristic of grasses. In comparison, only a single EST in Arabidopsis falls into the b-expansin family, which has a total of five b-expansin genes in its genome compared with 26 a-expansin genes. The large number of b-expansin genes in grasses is likely related to the fact that the cell wall matrix polysaccharides and structural proteins of grasses differ from those most other angiosperms. We suspect that __-expansins act on these unique wall components, such as the unique mixed-linked __1,3:1,4-glucan and glucuronoarabinoxylans found in grass species. This is supported by the fact that *Zea* m1 (=ExpB1 protein) has high specificity of action for grass cell walls over dicot cell walls. However, detailed biochemical tests of this hypothesis are needed, particularly for the b-expansins expressed in vegetative tissues.

Maize expansins are also notable, in comparison with the expansin family in *Arabidopsis*, because some of the b-expansins genes appear to be present in multiple copies of nearly identical genes, e.g. ExpB1a-c, ExpB2/8 and ExpB4. This is not the case in the Arabidopsis expansin gene family.

Our new data allow us to identify particular sequence characteristics that are common to both a- and b-expansins and that distinguish each group. The most notable features conserved in both groups of expansins include several sequence motifs, including the following: AT(F/W)YG (SEQ ID NO:9); GGACG (SEQ ID NO:10); CGSC; HFD and RVPC (SEQ ID NO:9) FIG. 1. Additionally, a set of 4 tryptophans at the carboxy terminus with conserved spacing is common to both a- and b-expansins, as is a set of six cysteine residues (b-expansins lack an additional pair of cysteines that are characteristic of a-expansins). In b-expansins the absence of 14 consecutive residues in the middle of the protein, including a pair of cysteines that are conserved in a-expansins, suggests the absence of a loop that is present in a-expansins and is stabilized by a disulfide bridge. The sequence analysis also suggests that b-expansins are glycosylated, whereas a-expansins are not.

This protein has a signal peptide (the first 24 amino acids) that directs the protein into the secretory pathway. The remainder of the protein has highly significant sequence similarity to beta-expansin sequences in GenBank, as seen in the following BLAST search result:

```
gi|8118425|gb|AAF72985.1|AF261272_1 (AF261272) beta-expansin
[Oryza sativa] (SEQ ID NO:12)
Length = 286, Query SEQ ID NO:2 24-282, Consensus SEQ ID NO:11
Score = 487 bits (1253), Expect = e-136
Identities = 231/265 (87%), Positives = 244/265 (91%), Gaps = 6/265 (2%)
```

```
                                                               -continued
Query:   24 CREAQFDAADAGAE------NFNTSEAAVYWGPWQKARATWYGQPNGAGPDDNGGACGRK   77
            C  A F+A DA A+        +FN+S+AAVYWGPW KARATWYGQPNGAGPDDNGGACGFK
Sbjct:   22 CAAADFNATDADADFAGNGWDFNSSDAAVYWGPWTKARATWYGQPNGAGPDDNGGACGFK   81

Query:   78 HTNQYPFMSMGSCGNQPLFKDGKGCGSCYKIRCRKDPSCSGRTETVIITDMNYYPVSKYH  137
            HTNQYPFMSM SCGNQPLFKDGKGCGSCYKIRC KD SCSGR+ETVIITDMNYYPV+ +H
Sbjct:   82 HTNQYPFMSMTSCGNQPLFKDGKGCGSCYKIRCTKDQSCSGRSETVIITDMNYYPVAPFH  141

Query:  138 FDLSGTAFGRLAKSGLNDKLRHSGIIDIEFTRVPCEFPGLKIGRHVEEYSSPVYFAVLVE  197
            FDLSGTAFGRLAK GLNDKLRHSGIIDIEFTRVPCEFPGLKIGFHVEEYS+PVYFAVLVE
Sbjct:  142 FDLSGTAFGRLAKPGLNDKLRHSGIIDIEFTRVPCEFPGLKIGFHVEEYSNPVYFAVLVE  201

Query:  198 YEDGDGDVVQVDLMESKTARGPPTGRWAPMRESWGSVWRMDTNHRMQPPFSIRIRNESGK  257
            YEDGDGDVVQVDLMESKTA GPPTG+W PMRESWGS+WR+DTNHR+Q PFSIRIRNESGK
Sbjct:  202 YEDGDGDVVQVDLMESKTAHGPPTGKWTPMRESWGSIWRLDTNHRLQAPFSIRIRNESGK  261

Query:  258 TLVARNVIPANWRPNTFYRSFVQYS                                    282
            TLVA NVIPANWRPNTFYRSFVQYS
Sbjct:  262 TLVANNVIPANWRPNTFYRSFVQYS                                    286

>gi|8118430|gb|AAF72987.1|AF261274_1 (AF261274) beta-expansin
[Oryza sativa] (SEQ 10 NO:14), Query SEQ ID NO:2 38-282, Consensus
SEQ ID NO:13
Length = 275
Score = 405 bits (1042), Expect = e-112
Identities = 190/245 (77%), Positives = 213/245 (86%)

Query:   38 NFNTSEAAVYWGPWQKARATWYGQPNGAGPDDNGGACGFKHTNQYPFMSMGSCGNQPLFK   97
            N+N S+A+ Y   W  ARATWYG P GAGPDDNGGACGFK+ NQYPF SM SCGN+P+FK
Sbjct:   31 NYNVSDASAYGSGWLPARATWYGAPTGAGPDDNGGACGFKNVNQYPFSSMTSCGNEPIFK   90

Query:   98 DGKGCGSCYKIRCRKDPSCSGRTETVIITDMNYYPVSKYHFDLSGTAFGRLAKSGLNDKL  157
            DGKGCGSCY+IRC KDPSCSG  ETVIITDMNYYPV++YHFDLSGTAFG +AK GLNDKL
Sbjct:   91 DGKGCGSCYQIRCNKDPSCSGNIETVIITDMNYYPVARYHFDLSGTAFGAMAKPGLNDKL  150

Query:  158 RHSGIIDIEFTRVPCEFPGLKIGFHVEEYSSPVYFAVLVEYEDGDGDVVQVDLMESKTAR  217
            RHSGIIDI+F RVPC +PGLKI FHVEE S+PVYFAVLVEYED DGDVVQVDLMESK+A
Sbjct:  151 RHSGIIDIQFRRVPCNYPGLKINFHVEEGSNPVYFAVLVEYEDLDGDVVQVDLMESKSAY  210

Query:  218 GPPTGRWAPMRESWGSVWRMDTNHRMQPPFSIRIRNESGKTLVARNVIPANWRPNTFYRS  277
            G  TG W PMRESWGS+WR+D+NHR+Q PFS+RIR++SGKTLVA NVIPANW PN+ YRS
Sbjct:  211 GGATGVWTPMRESWGSIWRLDSNHRLQAPFSLRIRSDSGKTLVANNVIPANWSPNSNYRS  270

Query:  278 FVQYS                                                         282
            VQ+S
Sbjct:  271 IVQFS                                                         275

At the nucleotide level a BLAST search also revealed sequence similarity
to known beta-expansins:
gi|8118424|gb|AF261272.1|AP261272 Oryza sativa beta-expansin (EXPB4)
mRNA, complete cds (SEQ ID NO:15), Query SEQ ID NO:1, 158-892
Length = 1249
Score = 942 bits (475), Expect = 0.0
Identities = 670/735 (91%)
Strand = Plus/Plus Query:   80 acttcaacaccagcgaggccgccgtgtactggggcccctggcagaaggcccgggccacct  139
            ||||||||| |||||| |||||||| |||||||||||||||   |||||| |||||||||
Sbjct:  188 acttcaactccagcgacgccgccgtctactggggcccctggaccaaggccagggccacct  247

Query:  140 ggtacggccagcccaacggcgccggcccggacgacaacggtggtgcgtgcggcttcaagc  199
            |||||||||||||||||||||||||||| ||||||||||||  || |||||| |||||||
Sbjct:  248 ggtacggccagcccaacggcgccggccccgacgacaacggcggcgcgtgcgggttcaagc  307

Query:  200 acaccaaccagtaccccttcatgtccatgggctcctgcggaaaccagccattgttcaagg  259
            |||||||||||||||| |||||||| || |||||||||| |||||||||||||||||||
Sbjct:  308 acaccaaccagtacccgttcatgtcgatgacctcctgcggcaaccagccattgttcaagg  367

Query:  260 acggcaagggatgcggctcctgctacaagattcggtgcaggaaggacccgtcctgctccg  319
            ||||||||||||||||||| ||||||||||| |  |||| |||  |||||| ||||||||
Sbjct:  368 acggcaagggatgcggctcttgctacaagatcagatgcaccaaggaccagtcgtgctccg  427

Query:  320 ggcggacggagacggtgatcatcaccgacatgaactactacccggtgtccaagtaccact  379
            |  || ||||||||||||||||||||||||||||||||||||||| || || ||||||
Sbjct:  428 gcaggtcggagacggtgatcatcaccgacatgaactactacccggtggctccgttccact  487

Query:  380 tcgacctcagcggcacggcgttcggcaggctggccaagtccggcctcaacgacaagctcc  439
            ||||||||||||||||||||||||||||| ||||| | ||||||||||||||||||||| |
Sbjct:  488 tcgacctcagcggcacggcgttcggcaggctcgccaagcctggcctcaacgacaagctgc  547
```

-continued

```
Query:  440 gccactcgggcatcatcgacatcgagttcaccagggtgccgtgcgagttccctggcctca 499
            |||||| ||||||||||||||||||||||||||||||||| ||||||||||||  | ||||
Sbjct:  548 gccactccggcatcatcgacatcgagttcaccagggtgccatgcgagttcccggggctca 607

Query:  500 agatcgggttccacgtggaggagtactcgagccccgtctacttcgcggtgctggtggagt 559
            ||||||||||||||||||||||||||||||||  ||| || |||||||||||||||||||
Sbjct:  608 agatcgggttccacgtggaggagtactcgaaccctgtgtacttcgcggtgctggtggagt 667

Query:  560 acgaggacggcgacggcgacgtggtgcaggtggacctgatggagtccaagacggcgcgcg 619
            |||||||||||||||||||||||||||||||||||||||||||||| |||||||||| ||
Sbjct:  668 acgaggacggcgacggcgacgtggtgcaggtggacctgatggagtcgaagacggcgcacg 727

Query:  620 ggccgccgacgggcgctgggcgccgatgcgcgagtcctggggctccgtctggcgcatgg 679
            ||||||||||||||  ||| ||||||||| |||||||| ||||||| |||||  | |||
Sbjct:  728 ggccgccgacggggaagtggacgccgatgagggagtcgtgggctccatctggaggctgg 787

Query:  680 acaccaaccaccgcatgcagccgcccttctccatccgcatccgcaacgagtccggcaaga 739
            ||||||||||| |    |  |||| | ||||||||||||||||||||||||||||||||
Sbjct:  788 acaccaaccacaggctccaggccccttctccatccgcatccgcaacgagtccggcaaga 847

Query:  740 cgctcgtcgccaggaacgtcatcccggccaactggaggcccaacaccttctaccgctcct 799
            |||||||||||| ||||||||||||||||||||||||||||||||| |||||||||||||
Sbjct:  848 cgctcgtcgccaacaacgtcatcccggccaactggaggcccaacacattctaccgctcct 907

Query:  800 tcgtccagtacagct 814
            |||||||||||||||
Sbjct:  908 tcgtccagtacagct 922
```

> gi|11346545|gb|AF261276.2|AF261276 Oryza sativa beta-expansin
(EXPB8) mRNA, partial cds (SEQ ID NO:16), SEQ ID NO:1, 417
Length = 933
Score = 178 bits (90), Expect = 3e-42
Identities = 216/258 (83%)
Strand = Plus / Plus

```
Query:  339 catcaccgacatgaactactacccggtgtccaagtaccacttcgacctcagcggcacggc 398
            |||||||||||||||||||| ||   ||| |||||||||||||||||||||||||||  |
Sbjct:  348 catcaccgacatgaactacttcccctctcccagtaccacttcgacctcagcggcatcgc 407

Query:  399 gttcggcaggctggccaagtccggcctcaacgacaagctccgccactcgggcatcatcga 458
            |||||  || || || ||||| |||| |  ||  | ||||| | ||| |||||||||||
Sbjct:  408 cttcggccgcctcgccaagcccggccgcgccgacgacctccgcgcgcgcgggatcatcga 467

Query:  459 catcgagttcaccagggtgccgtgcgagttccctggcctcaagatcgggttccacgtgga 518
            || |     ||||   |||||||||||||||||| ||||| ||| |||||||||||||||
Sbjct:  468 cgtgcagttcgcgcgcgtgccgtgcgagttcccgggcctcaaggtgggattccacgtgga 527

Query:  519 ggagtactcgagccccgtctacttcgcggtgctggtggagtacgaggacggcgacggcga 578
            |||       ||||||||| ||  | ||||||||||||||||||||||   |||||| ||
Sbjct:  528 ggaagggtccagccccgtgtacctggcggtgctggtggagtacgagaacggcgacggaga 587

Query:  579 cgtggtgcaggtggacct 596
            |||| ||||||||||||
Sbjct:  588 cgtggcgcaggtggacct 605
```

Score = 99.6 bits (50), Expect = 2e-18
Identities = 140/170 (82%)
Strand = Plus / Plus SEQ ID NO:17

```
Query:  641 cgccgatgcgcgagtcctggggctccgtctggcgcatggcaccaaccaccgcatgcagc 700
            |||||||||| |||||| |||||| |||| |  | | |   |||| ||||||||| | |
Sbjct:  638 cgccgatgcgggagtcgtgggggtcggtgtggaggctggactccaaccaccgcctgcggg 697

Query:  701 cgcccttctcctccgcatccgcaacgagtccggcaagacgctcgtcgccaggeecgtca 760
            |||| ||||| |||||||||||| ||||||||||||||| ||||| |  |||  |||||
Sbjct:  698 cgccattctccatccgcatccggagcgactccggcaagacgttggtggcacccgccgtca 757

Query:  761 tcccggcceactggeggcccaacaccttctaccgctccttcgtccagtac 810
            ||||   ||||||| ||||||||||||| ||||||||||||||||||||
Sbjct:  758 tccccctcaectggacgcccaecaccttttccgttccttcgtccagtac 807
```

Score = 69.9 bits (35), Expect = 2e-09
Identities = 119/147 (80%)
Strand = Plus / Plus SEQ ID NO:18

```
Query:  139 tggtccgccagcccaacgcgccggcccggcgcaccggtggtgcgtgcgcttcag 198
            |||||| ||| |||||||| |||||||   ||||| ||||||  |||||||||||
Sbjct:  148 tggtacgggcegccgaacggcgccggggcggcggacaacggcggggcgtgcgggttcceg 207
```

-continued

```
Query:  199 cacaccaccegtecccettcctgtccatgggctcctgcggeeeccegccettgttcaeg  258
            |   ||||||||||||  ||||||   |||   ||  |||||  ||||||||    |||  ||||
Sbjct:  208 aaggtgaaccegtecccgttcatggggatgacgtcgtgcgggeaccagccgctgtaceag  267

Query:  259 gacggcaagggatgcggctcctgctac                                   285
            |  |||||||||||  ||||||||||||||||
Sbjct:  268 ggcggcaagggctgcggctcctgctac                                   294
```

Expression of Zm-ExpB2 is very broad and very high (see FIG. 1). The high level of expression indicates that this beta-expansin may be the beta-expansin family member with the greatest and most widespread influence on expansin-mediated processes, such as cell enlargement, cell wall plasticity, and the rheological properties of maize cell walls (e.g. in leaves, stems, roots, silks, and other organs). Thus, this sequence could be most useful in modifying these plant characteristics, e.g. by increasing expression by inserting the maize a suitable recombinant DNA construct with an appropriate promoter that drives the expression of Zm-ExpB2. Alternatively, decreased expression of the endogenous Zm-ExpB2 gene might be obtained by identification of plants with defective Zm-ExpB2 genes or by transgenic methods employing antisense, co-suppression, double-stranded RNA, or other gene silencing methods, employing either the conserved regions of ExpB2 or the gene-specific parts of ExpB2.

The predicted ExpB4 protein has a signal peptide that directs the protein into the secretory pathway. The remainder of the protein has highly significant sequence similarity to beta-expansin sequences in GenBank, as seen in the following BLAST search result:

```
gi|8118428|gb|AAF72986.1|AF261273_1 (AF261273) beta-expansin
[Oryza sativa] SEQ ID NO:20
Length = 275 Consensus SEQ ID NO:19, Query SEQ ID NO:4
Score = 261 bits (668), Expect = 7e-69
Identities = 138/249 (55%), Positives = 180/249 (71%), Gaps = 5/249 (2%)

Query:   40 RNHTATPTPSPTVYGPGGWLSXXXXXXXXXXXNGDGSDGGACGYQTAVGKKPFDSMIAAGS   99
            +N+TA +++ GW S    GDGS+GGACGYQ+AVG++PF SMIAAG
Sbjct:   27 QNYTAGRRSTMSLGRGYGW-SSGGATWYGGPQGDGSEGGACGYQSAVGQRPFSSMIAAGG   85

Query:  100 TPLYRGGEGCGACYEVKCTTNAACSGQPVTIVITDQSPGGLFPGEVEHFDMSGTAMGAMA  159
            L++G+GCG+CY++KCT N ACSG+PVT+VITD PGG+ E HFDMSGTA GAMA
Sbjct:   86 PSLFKNGKGCGSCYQIKCTGNRACSGRPVTVVITDSCPGGVCLNEAAHFDMSGTAFGAMA  145

Query:  160 RPGMADKLRAGGVLRILYRRVPCKYTGVNIAFKVDQGANPYYFDVLIEFEDDDGDLSAVD  219
            GM D+LR+GVL+I Y+RVPC++ +N+AFKVD G+NPYY +L++++DGDL+AV
Sbjct:  146 NRGMGDRLRSAGVLKIQYKRVPCRF-AMNVAFKVDAGSNPYYAILVQYANGDGDLAAVH  204

Query:  220 LMEA-GSGVWTPMAHNWGATWRLNN--GRKLKAPFGLRLTSDSRRVLVANNAIPAAWKPG  276
            +M+A  G G W M +WGATWRLN+ G+L PF+RLTS S+VLVANN IP+W G
Sbjct:  205 IMKARGGGGWKAMQQSWGATWRLNSNTGKPLSPPFSIRLTSGSGKVLVANNVIPSGWQAG  264

Query:  277 KTYRSLVNY  285
            TYRS VNY
Sbjct:  265 LTYRSTVNY  273

<
gi|8118432|gb|AAF72988.1|AF261275_1 (AF261275) beta-expansin
[Oryza sativa] SEQ ID NO:22
Length = 327 Consensus SEQ ID NO:21, Query SEQ ID NO:4
Score = 206 bits (525), Expect 3e-52
Identities 118/304 (38%), Positives = 173/304 (56%), Gaps 25/304 (8%)

Query:    2 CTRKLNKPKPKPG--------SYRRXXXXXXXXXXTGSYKPAPVAARRNHTATPTPSPTVY   53
            C+K+KPKP PG    S          AP +  + +
Sbjct:   28 CSAKHHKPKPTPGGISGNASSSSSNSSTPSIPPPVAPTPTAPTPPIPSPGTGSSNGSSGG   87

Query:   54 GPGGWLSXXXXXXXXXXXXNGDGSD--GGACGYQTAVGKKPFDSMIAAGSTPLYRGGEGCGA  111
            G GGWL+      NG G D GGACG++ V PF+M+G+PL++G+GCG+
Sbjct:   88 GGGGWLN-ARATWYGAPNGAGPDDNGGACGFKN-VNLPPFSAMTSCGNEPLFKDGKGCGS  145

Query:  112 CYEVKCTTNAACSGQPVTIVITDQSPGGLFPGEVEHFDMSGTAMGAMARPGMADKLRAGG  171
            CY+++C +ACSG PT++ITD+ +P +HFD+SGTA GAMA+ D+LR G
Sbjct:  146 CYQIRCVGHPACSGLPETVITDMN---YYPVSLYHFDLSGTAFGAMAKDNRNDELRHAG  202

Query:  172 VLRILYRRVPCKYTGVNIAFKVDQGANPYYFDVLIEFEDDDGDLSAVDLMEA--------  223
            ++I+RRVPC+Y G++FV+QG+NPY +L+E+E+DGD+ VDLME+
Sbjct:  203 IIDIQFRRVPCQYPGLTVTFHVEQGSNPVYMAILVEYENGDGDVVQVDLMESRYSTGGVD  262

Query:  224 --GSGVWTPMAHNWGATWRLNNGRKLKAPFGLRLTSDSRRVLVANNAIPAAWKPGKTYRS  281
            +GVWTPM +WG+ WRL+ L+PF LR+T++S+L+A+ IPA W+P YS
Sbjct:  263 GTPTGVWTPMRESWGSIWRLDTNHPLQGPFSLRITNESGKTLIADQVIPADWGPNTVYSS  322
```

```
Query: 282  LVNY  285
            +V+
Sbjct: 323  IVQF  326
```

Expression of Zm-ExpB4 is principally in the husk leaves, the silks and the ear. This pattern of expression suggests that this beta-expansin is likely important for the growth and cell wall properties of these organs, e.g. cell enlargement, cell wall plasticity, and the rheological properties of cell walls. Thus, this sequence could be most useful in modifying these plant characteristics, e.g. by increasing expression by inserting into maize a suitable recombinant DNA construct with an appropriate promoter that drives the expression of Zm-ExpB4. Alternatively, decreased expression of the endogenous Zm-ExpB4 gene might be obtained by identification of plants with defective Zm-ExpB2 genes or by transgenic methods employing antisense, co-suppression, double-stranded RNA, or other gene silencing methods, employing either the conserved regions of ExpB4 or the gene-specific parts of ExpB4.

Example 2

Expansin Activity Assays

Method of assaying for expansins activity are disclosed in Cosgrove, D. J. (1989) *Planta* 177:121–130. For creep reconstitution experiments, 1-cm segments were cut from the apical growing region, frozen at −20 C, thawed, abraded with carborundum slurry, heat inactivated and clamped in constant-load extensometers, as described previously (Cosgrove 1989). To compensate for the varvin2 thickness of the wall specimens, 5-g weights were used to keep the silk walls under constant tension, whereas 20-g weights were used for the coleoptile and hvpocotyl walls. For the stress relaxation measurements, the walls were pretreated for 10 min in either buffer or maize pollen extract, then stored on ice prior to extension and stress-relaxation measurements (Cosgrove 1989). Maximal force equivalents for the stress relaxation assays were 5 for silks, 20 g for coleoptile and hypocotyls.

To test whether an expansin may loosen or expand cell walls. Applicant may extract protein from maize (*Zea mays*) pollen or other plant, and assay its effects on the wall rheology of maize silks, which are the receptive stigmas and styles of the maize flower. Maize was used for these experiments because it is easy to collect large quantities of maize pollen and because the large size of the maize silk facilitates rheological assays. For these assays, silk walls were prepared so as to inactivate endogenous proteins and they were then clamped either at constant force to measure extension behavior or at constant extension to measure stress relaxation behavior (McQueen-Mason 1994; Li-1993).

Addition of the maize pollen extract induced rapid, irreversible extension (creep) of the silk walls when tested in constant-force extensometers. Likewise, the pollen extract enhanced stress relaxation of the silk walls over a large range of times.

Both of these rheological effects are unique characteristics of expansion action (McQueen-Mason 1992; McQueen-Mason 1995; Cosgrove 1996). Moreover, these rheological effects required an acidic pH (<5.5), likewise similar to the action of expansins.

While the invention has been particularly shown and described with reference to preferred embodiments thereof, it will be understood by those skilled in the art that various alterations in form and detail may be made therein without departing from the spirit and scope of the invention.

---

What is claimed is:

1. A method of making a beta expansin protein comprising the steps of:
   A) expressing a protein encoded by a polynucleotide in a recombinantly engineered cell, wherein the polynucleotide is selected from the group consisting of:
      (a) a polynucleotide encoding a B2 beta expansin polypeptide of the sequence shown in SEQ ID NO:1;
      (b) a polynucleotide which encodes the polypeptide sequence shown in SEQ ID NO:2, and
      (c) a polynucleotide having at least 90% sequence identity with polynucleotides of (a) or (b) and having the beta expansin protein activity of altering cell wall mechanical strength;
   said polynucleotide operably linked to a promoter; and
   B) purifying the protein.

2. A method of making a beta expansin protein comprising the steps of:
   A) expressing a protein encoded by a polynucleotide in a plant, wherein said polynucleotide is selected from the group consisting of:
      (a) a polynucleotide encoding a B2 beta expansin polypeptide of the sequence shown in SEQ ID NO:1;
      (b) a polynucleotide which encodes the polypeptide sequence shown in SEQ ID NO:2;
      (c) a polynucleotide having at least 90% sequence identity with polynucleotides of (a) or (b); and having the beta expansin protein activity of altering cell wall mechanical strength; and
   B) purifying the protein from the plant seed or other plant parts.

3. An isolated polypeptide having expansin activity of altering cell wall mechanical strength and selected from the group consisting of:
   (a) a polypeptide comprising the amino acid sequence set forth in SEQ ID NO:2;
   (b) a polypeptide encoded by a nucleotide sequence comprising the sequence set forth in SEQ ID NO:1;
   (c) a polypeptide encoded by a nucleotide sequence that has at least 90% sequence identity to the sequence set forth in SEQ ID NO: 1; and
   (d) a polypeptide comprising an amino acid sequence having at least 90% sequence identity to the sequence set forth in SEQ ID NO:2.

* * * * *